(12) United States Patent
Wong et al.

(10) Patent No.: US 11,497,710 B2
(45) Date of Patent: *Nov. 15, 2022

(54) EYE DROP FORMULATION AND METHOD FOR SUSTAINED DELIVERY OF MEDICAMENT TO THE RETINA

(71) Applicant: Chibi, Inc., Menlo Park, CA (US)

(72) Inventors: Vernon G. Wong, Menlo Park, CA (US); Glenn T. Huang, Fremont, CA (US)

(73) Assignee: CHIBI, INC., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/909,591

(22) Filed: Jun. 23, 2020

(65) Prior Publication Data

US 2020/0368153 A1 Nov. 26, 2020

Related U.S. Application Data

(63) Continuation of application No. PCT/US2019/030290, filed on May 1, 2019.

(60) Provisional application No. 62/665,273, filed on May 1, 2018.

(51) Int. Cl.

| A61K 9/00 | (2006.01) |
|---|---|
| A61K 31/4709 | (2006.01) |
| A61K 31/569 | (2006.01) |
| A61K 31/573 | (2006.01) |
| A61K 47/14 | (2017.01) |
| A61K 47/22 | (2006.01) |
| A61K 9/08 | (2006.01) |

(52) U.S. Cl.
CPC ........ A61K 9/0048 (2013.01); A61K 31/4709 (2013.01); A61K 31/569 (2013.01); A61K 31/573 (2013.01); A61K 47/14 (2013.01); A61K 47/22 (2013.01); A61K 9/08 (2013.01)

(58) Field of Classification Search
CPC .... A61K 9/0048; A61K 31/573; A61K 47/22; A61K 9/08
See application file for complete search history.

(56) References Cited

U.S. PATENT DOCUMENTS

| 5,869,079 A * | 2/1999 | Wong ..................... A61K 47/34 424/426 |
|---|---|---|
| 6,331,313 B1 | 12/2001 | Wong et al. |
| 7,906,136 B2 | 3/2011 | Wong et al. |
| 8,470,873 B2 | 6/2013 | Chen |
| 8,541,413 B2 | 9/2013 | Wong et al. |
| 8,722,728 B2 | 5/2014 | Wong et al. |
| 8,957,110 B2 | 2/2015 | Aleo et al. |
| 9,011,915 B2 | 4/2015 | Wong et al. |
| 9,144,566 B2 | 9/2015 | Wong et al. |
| 9,289,428 B2 | 3/2016 | Wong et al. |
| 9,474,736 B2 | 10/2016 | Wong et al. |
| 9,585,959 B2 * | 3/2017 | Tiberg .................... A61K 47/24 |
| 9,737,606 B2 | 8/2017 | Wong et al. |
| 9,814,773 B2 | 11/2017 | Wong et al. |
| 9,993,558 B2 | 6/2018 | Wong et al. |
| 10,744,202 B2 | 8/2020 | Wong et al. |
| 2006/0073182 A1 | 4/2006 | Wong et al. |
| 2008/0085263 A1 | 4/2008 | Thuresson et al. |
| 2008/0260832 A1 | 10/2008 | Burke et al. |
| 2013/0017244 A1 | 1/2013 | Huang et al. |
| 2015/0343071 A1 | 12/2015 | Vangara et al. |
| 2018/0000729 A1 * | 4/2018 | Tamraz ................... A61K 9/00 |
| 2020/0368152 A1 | 11/2020 | Wong et al. |

FOREIGN PATENT DOCUMENTS

EP 3272362 A1 1/2018

OTHER PUBLICATIONS

Pubchem, Compound Summary, Decanoyl/octanoyl-glycerides, date: Feb. 16, 2015 (Year: 2015).*
Jay S. Duker, Sustained-release drug delivery products edge closer to fruition, Healio, publication date: May 3, 2016 (Year: 2016).*
PCT Application No. PCT/US2019/030290, International Preliminary Report on Patentability dated Nov. 12, 2020, 7 pages.
International Search Report for PCT/US2019/030290, dated Aug. 22, 2019, 4 pages.
European Patent Office, Extended European Search Report, European Patent Application No. 19796932.2, dated Dec. 7, 2021, 7 pages.

* cited by examiner

*Primary Examiner* — Mark V Stevens
*Assistant Examiner* — Alparslan Asan
(74) *Attorney, Agent, or Firm* — Kilpatrick Townsend & Stockton LLP

(57) ABSTRACT

The present embodiments provide compositions, methods and kits for the treatment of ocular conditions or maladies affecting the back of the eye, e.g., the retina.

11 Claims, 7 Drawing Sheets

EYE DROP FORMULATION AND METHOD FOR SUSTAINED DELIVERY OF MEDICAMENT TO THE RETINA

RELATED APPLICATION

The present application is a continuation of International Application No. PCT/US2019/030290, filed May 1, 2019, which claims priority benefit of U.S. Provisional Application No. 62/665,273, filed May 1, 2018, the disclosures of which are hereby incorporated by reference in their entirety for all purposes.

FIELD

The present embodiments provide compositions and methods for the treatment of ocular conditions or maladies affecting the back of the eye, e.g., the retina.

BACKGROUND

There remains a need for noninvasive, sustained delivery of pharmaceutical agents to tissues and liquid portions in the back of the eye, such as the retina or vitreous body.

SUMMARY

The present embodiments provide compositions and methods for treating or preventing ocular ailments via a non-invasive liquid depot that delivers at least one pharmaceutical agent to the eye for days or weeks. This liquid depot is biocompatible and adapts to the shape of the eye, forming a thin film or flat bubble that covers the exterior tissues of the eye (e.g., conjunctiva, corneal surface) and is resistant to lacrimation (e.g., tears); although this film remains in place for days or over a week during the delivery of pharmaceutical agent(s), it does not impair vision after initial instillation; and instillation of the liquid depot is mediated, at least in part, by viscosity of the liquid depot. Remarkably, although this liquid depot remains on the outside of the eye, pharmaceutical agent(s) is delivered to interior ocular tissues (e.g., retina) and fluids (e.g., the vitreous humor) in the back the eye for at least three (3) days, and in some embodiments at least seven (7) days. As such, effective intermittent administration (e.g., once every 3 days or longer) of a single-dose liquid depot comprising at least one pharmaceutical agent is made possible with the present embodiments, in marked contrast to the typical multiple daily doses currently required with conventional commercial ocular formulations.

The liquid depot described herein provides sustained release of pharmaceutical agent(s) at a steadier release rate (i.e., decreased "spike"), fewer side effects, and/or superior efficacy compared with current aqueous-based eye drops. In some embodiments, the continuous levels of pharmaceutical agent released from the liquid depot of the present embodiments provides efficacious benefit at $C_{max}$ concentrations of pharmaceutical agent below those previously thought to be required to achieve clinical benefit, based on comparison with current aqueous-based eye drops.

Figure 10:
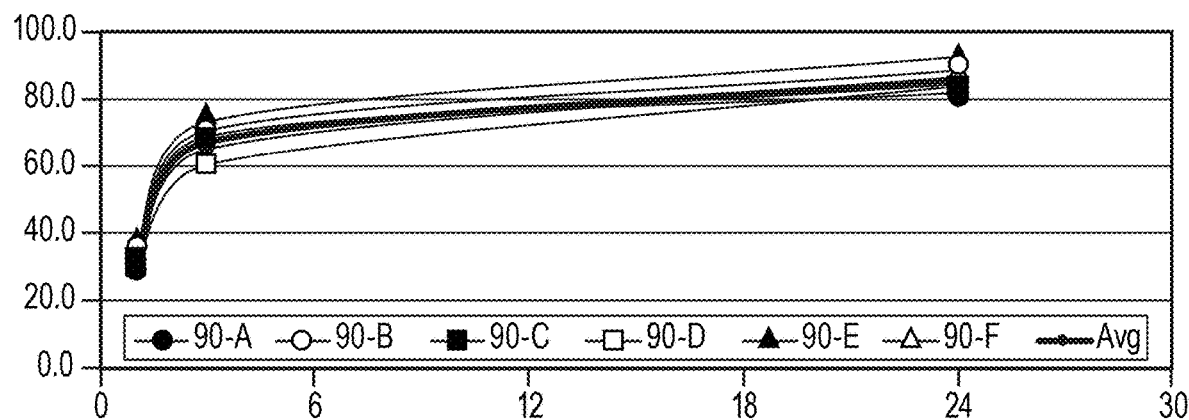

FIG. 10 is a graph showing in vitro release of gatifloxacin from a gatifloxacin-containing liquid depot formulation (10% gatifloxacin and 90% of a mixture of tocopheryl acetate:Miglyol® 810 (medium chain triglycerides) at a wt/wt ratio of about 70:30). Twenty mL of each sample were withdrawn for sampling and replaced with 20 mL of saline. Six replicates were tested: y-axis, % gatifloxacin released; x-axis, hours; ●: 90-A; ○: 90-B; ■: 90-C; □: 90-D; ▲: 90-E; Δ: 90-F; •: Avg.

Figure 11:
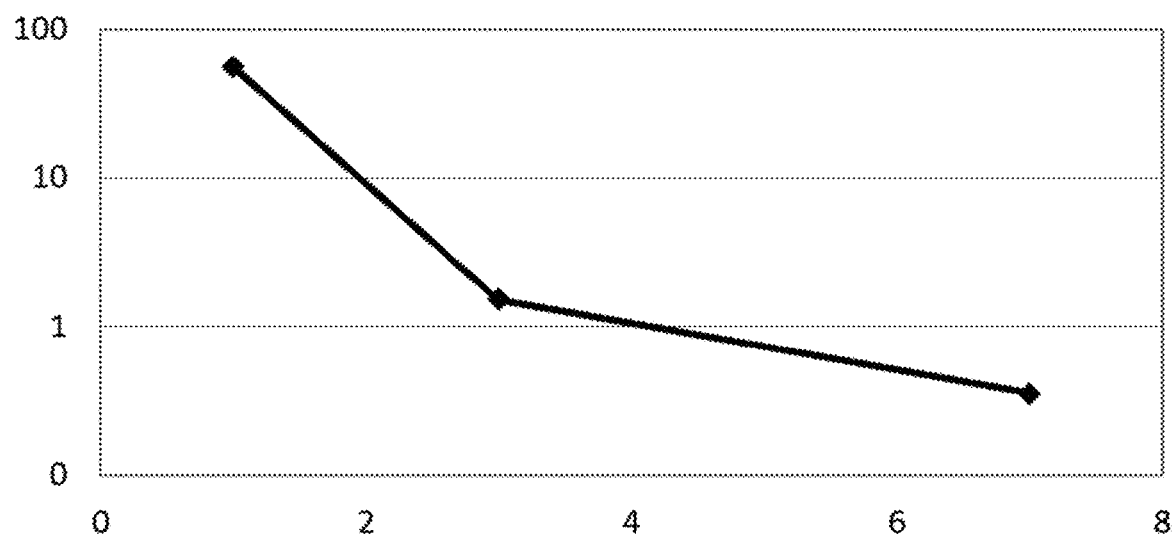

FIG. 11 is a graph showing results of an in vivo PK study of diclofenac acid drug level in tear samples. y-axis: ng diclofenac/mg tear; x-axis: day.

Figure 12:
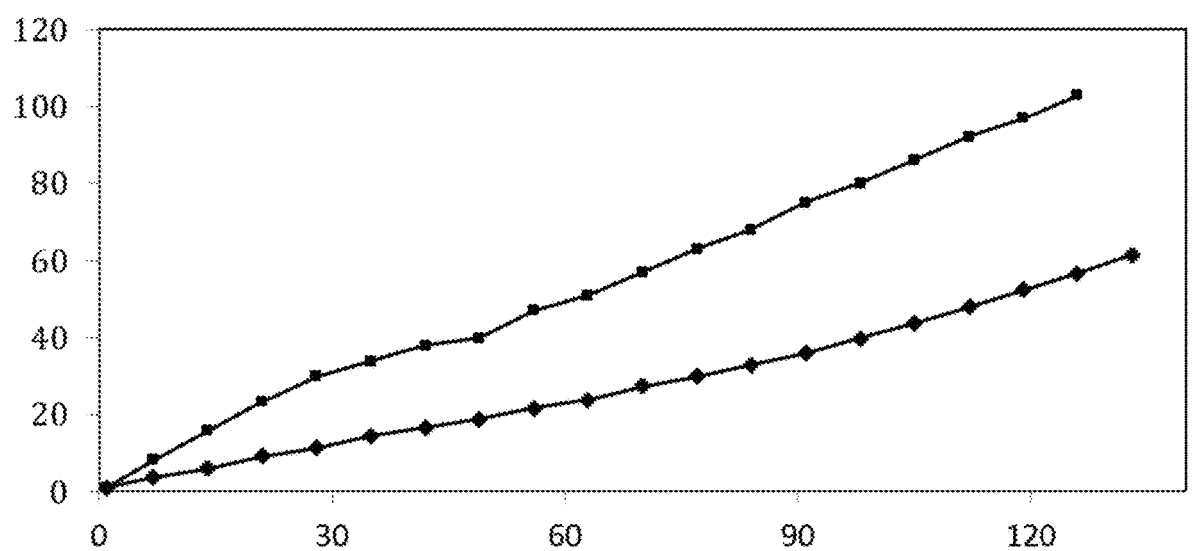

FIG. 12 is a graph showing in vitro release of cyclosporin from two liquid depots containing 2% cyclosporine in an excipient mixture of either 90:10 tocopheryl acetate:Miglyol® 812 (♦) or 70:30 tocopheryl acetate:Miglyol® 812 (■). y-axis: cyclosporin A total release, %; x-axis: days.

DETAILED DESCRIPTION

It should be understood that this invention is not limited to the particular methodology, protocols, and reagents, etc., described herein and as such may vary. The terminology used herein is for the purpose of describing particular embodiments only and is not intended to limit the scope of the present invention, which is defined solely by the claims.

All patents and other publications identified are incorporated herein by reference for the purpose of describing and disclosing, for example, the methodologies described in such publications that might be used in connection with the present invention but are not to provide definitions of terms inconsistent with those presented herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on information available to the applicants and do not constitute any admission as to the correctness of the dates or contents of these documents.

As used herein and in the claims, the singular forms "a," "an," and "the" include the plural reference unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either." Thus, unless context indicates otherwise, the word "or" means any one member of a particular list and also includes any combination of members of that list. Other than in the operating examples, or where otherwise indicated, all numbers expressing quantities of ingredients or reaction conditions used herein should be understood as modified in all instances by the term "about" which generally allows variation of ±1 unless context dictates otherwise. In general, and unless otherwise indicated or clarified by context, amounts or levels presented as "%" are based on weight (i.e., wt % or wt/wt).

Headings are provided for convenience only and are not to be construed to limit the invention in any way. Unless defined otherwise, all technical and scientific terms used herein have the same meaning as those commonly understood to one of ordinary skill in the art. The terminology used herein is for the purpose of describing particular embodiments only and is not intended to limit the scope of the present invention, which is defined solely by the claims. In order that the present disclosure can be more readily understood, certain terms are first defined. Additional definitions are set forth throughout the detailed description.

Figure 1A:
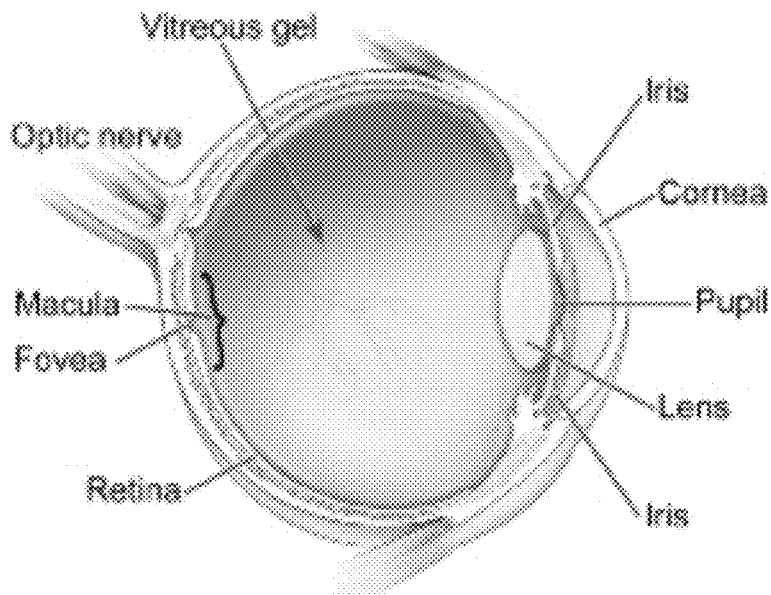
FIGS. 1A and 1B are illustrations of human eye anatomy, more specifically representing a left eye (1A) and a right eye (1B) viewed from above. The back of the eye generally includes the retina, including the macula, and the vitreous humor (vitreous body or vitreous gel).
Figure 1B:
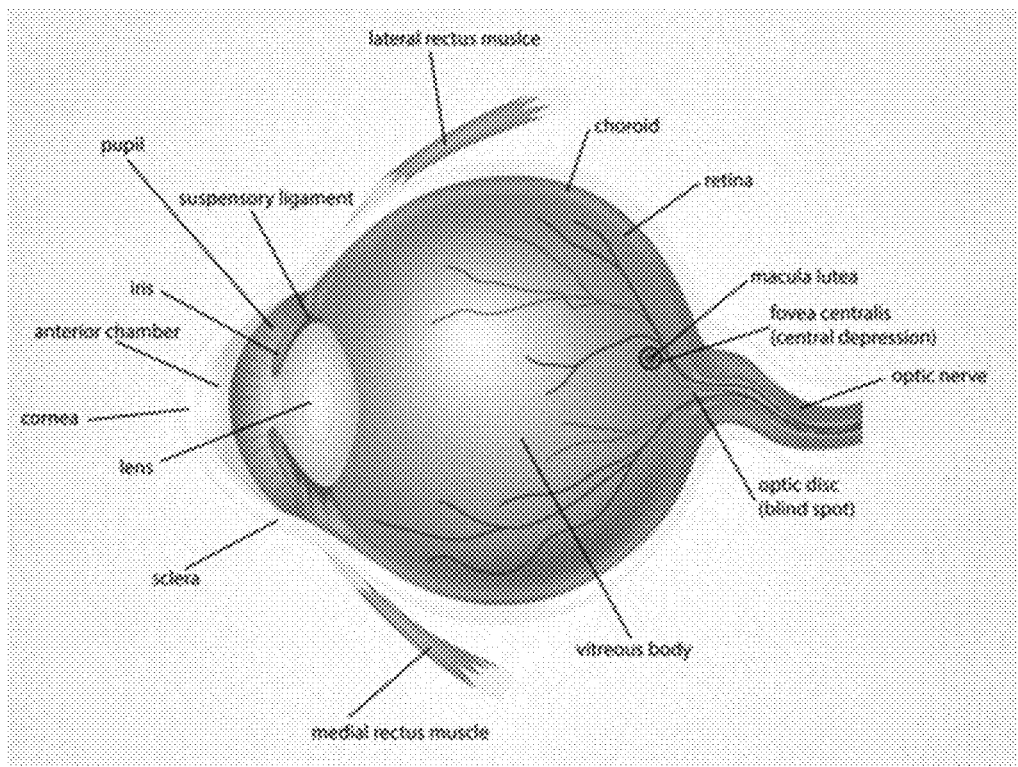

Maladies affecting the back of the eye, e.g., the retina (see FIG. 1A and FIG. 1B), are difficult to treat. Retinal diseases can be related to aging, diabetes or other diseases, trauma to the eye, or family history. Treatment of retinal disease may be complex and sometimes urgent, in which the main treatment goals are to stop or slow disease progression and preserve, improve, or restore vision. For example, diabetic retinopathy occurs when existing or new, abnormal capillaries in the back the eye deteriorate and leak fluid into and under the retina, which causes the retina to swell. Scatter laser photocoagulation is one technique used to shrink these blood vessels, but extensive use of this treatment may result in loss of peripheral or night vision. Because capillary formation and leakage are associated with inflammation, anti-inflammatory agents are beneficial in treating diabetic retinopathy as well as macular degeneration. Hence, injecting medication, such as steroid, into the vitreous in the eye is another technique for treating retinal disease, including diabetic retinopathy, macular degeneration, cystoid macular edema, or broken blood vessels within the eye. Sustained release injectable and implantable formulations are becoming important options in medicating the eye. Injection into the eye is not without risk, however, and must be done with at least local anesthetic, aseptic technique, by a skilled ophthalmologist. Accordingly, topical formulations that can effectively deliver pharmaceutical agents into tissues and fluids in the back of the eye clearly represent a long-felt but unmet need in the art.

Currently available topical formulations used in ophthalmology include aqueous solutions, aqueous suspensions, ointments, and inserts. In current eye drop formulations, however, transcorneal transport (i.e., drug penetration into the eye) is not an effective process, as an estimated one-tenth of a dose penetrates into the eye. Moreover, current commercially available eye drops do not provide sustained release over extended periods of time, e.g., over the course of days. In contrast to current commercially available ophthalmic formulations, the present embodiments provide a liquid depot that quickly forms a film over the eye that is not blinked away and does not impair vision, except fleetingly at the time of administration. Further, without being bound by theory, because the present liquid depot delivers active agent to ocular tissues, at least some ocular tissues serve as repositories for active agent, prolonging release or therapeutic benefit. Importantly and surprisingly, the present embodiments provide effective, efficient, and sustained delivery of pharmaceutical agents to the back of the eye, e.g., the retina, via a topical liquid depot.

Additionally, the sustained-release liquid depot has a physical consistency that avoids running, and allows the patient to wear eye makeup, and comfortably wear contact lenses. Because of long-lasting release and therapeutic benefit, the liquid depot can be supplied in a single-administration dispenser that is easy to use because the patient (or health care provider) can focus all their attention to dispensing the formulation into the eye without diverting attention to avoiding all contact with the tip of the dispenser. Also, the present embodiments enable instillation from a single-use dispenser such that preservative is not required in the formulation. Accordingly, at least one embodiment provides a single-use dispenser comprising a unit dosage of the liquid depot. Further embodiments provide a kit or kits comprising at least one single-use dispenser preloaded with a single dosage unit, i.e., a single liquid depot.

More specifically, ophthalmic products must be sterile in the final container to prevent microbial contamination of the eye. Whether current ocular therapies are formulated as solution, suspension, or ointment, most current formulations are administered from droppers or tubes that must be used with care to avoid allowing the tip of the dropper or tube to touch the eyelid or any other surface that can contaminate the dispenser. Contamination of a dropper, solution, suspension, or the tip or cap of the tube, can lead to serious eye infection. Generally, preservatives are added to current eye drop formulations to maintain sterility once the container has been opened. The FDA Advisory Review Panel on OTC Ophthalmic Drug Products (1979) established preservatives and concentrations for use in formulations that will have direct contact with the eye. Many of these preservatives, however, react with active agents or plastics, or increase irritation of the eye drop. Because the present liquid depot provides sustained release and therapeutic benefit, in at least one embodiment the liquid depot can be supplied advantageously in an easy to use single-administration dispenser requiring no preservatives.

Additionally, oxygen sensitivity of many pharmaceutical agents results in instability. For this reason, current eye drops often include preservatives, such as sodium bisulfate, to increase stability of such active agents. The sustained-release liquid depot described herein is capable of releasing the active agent at therapeutic levels, for at least about 24 hours, more preferably, at least about 48 hours, and still more preferably, at least about 72 hours (3 days), even though the depot is exposed to oxygen from atmospheric exposure and constant washing from fluids in the eye. It is unexpected that an active agent remains stable over the course of delivery, e.g., for at least 3 days. Without being bound by theory, the stability observed in these embodiments may be due to the antioxidant nature of tocopherols or tocotrienols that is not unduly diluted or reduced by the presence of an ocular film-forming excipient.

At least one embodiment comprises at least one agent presented in a sustained-release liquid depot comprising, consisting of, or consisting essentially of a biocompatible and biodegradable mixture of tocopherol and an ocular film-forming excipient that has low solubility in aqueous solution.

In at least one embodiment, the sustained-release liquid depot comprises at least one active agent, about 60% to 90% (wt %) tocopherol (such as tocopheryl acetate), and about 10% to 40% (wt %) of an ocular film-forming excipient (such as decanoyl/octanoyl glycerides). In at least one embodiment, the liquid depot comprises about 70% to 85% (wt %) tocopherol (such as tocopheryl acetate), and about 15% to 30% (wt %) of an ocular film-forming excipient (such as decanoyl/octanoyl glycerides). In at least one embodiment, the liquid film-former excipient modulates (e.g., either increases or decreases) the viscosity of the liquid depot. For example, a liquid depot includes 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90% (wt %), or any interval therebetween, of tocopherol; and includes 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% (wt %), or any interval therebetween, of ocular film-forming excipient. In at least one embodiment, the film-forming excipient is a triglyceride. In at least one embodiment, the triglyceride is MIGLYOL® medium-chain triglycerides. In at least one embodiment, the active agent is dexamethasone. In at least one embodiment, the liquid depot consists essentially of (a) 10%-30% (wt %) dexamethasone; and (b) about 70%-90% (wt %) of a mixture of tocopheryl acetate:medium-chain triglycerides at a wt/wt ratio of about 85:15 to about 70:30.

Regarding viscosity, this characteristic describes the resistance to deformation exhibited between molecules moving in a fluid, or a form of internal friction that resists a fluid's flow when stress is applied. The viscosity of a solution is often given in poise (P), centipoise (cP), or millipascal seconds (mPa s). For example, at 20° C. water has a viscosity of 1.00 mPa s, or 1.00 cP, whereas motor oil (SAE 40) has a viscosity of 319 mPa s. Many fluids exhibit less viscosity when heated: for example, at 25° C., water has a viscosity of 0.890 mPa s. See, e.g., Elert, PHYSICS HYPERTEXTBOOK (1998-2017). Generally, current aqueous-based eye drop solutions have viscosity ranging from 25 cP to 50 cP (at 20° C.); and some of these ophthalmic solutions may include viscosity enhancers added to increase viscosity and perhaps enable the solution to remain longer in the eye. Typical compounds added to enhance viscosity in current eye drops are available in various grades such as 15 cP, 100 cP, etc., and include compounds such as methylcellulose, hydroxyethylcellulose, hydroxypropylmethyl-cellulose, polyvinyl alcohol, and polyvinylpyrrolidone. In preferred embodiments, none of these viscous-enhancing compounds are included in the liquid depot described herein.

In one embodiment, a sustained-release liquid depot, according to the subject invention, consists of tocopheryl acetate, MIGLYOL®, and dexamethasone having a viscosity of 850 cP to 1100 cP, such as about 850, 851, 852, 853, 854, 855, 856, 857, 858, 859, 860, 899, 990, 994, 995, 996, 997, 998, 999, 1000, 1001, 1002, 1003, 1004, 1005, 1006, 1007, 1007, 1008, 1009, 1010, 1011, 1020, 1021, 1022, 1023, 1024, 1025, 1026, 1027, 1028, 1029, 1030, 1031, 1032, 1075, 1076, 1077, 1078, 1079, 1080, 1081, 1082, 1083, 1099, or 1100 cP, inclusive of any cP therebetween. In another embodiment, a sustained-release liquid depot, according to the subject invention, consists of tocopheryl acetate, MIGLYOL® and dexamethasone having a viscosity of about 1027 cP. In another embodiment, a sustained-release liquid depot, according to the subject invention, consists of tocopheryl acetate, MIGLYOL®, and dexamethasone having a viscosity of 1027 cP±32 cP.

In at least one embodiment, the sustained-release liquid depot comprises, consists of, or consists essentially of a tocopherol and an ocular film-forming excipient. As used herein, "tocopherol" includes tocopherols, tocotrienols, esters thereof, and mixtures thereof. Tocopherol is commonly known as "vitamin E." See, e.g., WO2014100327; Lee et al., *Methods for efficient analysis of tocopherols, tocotrienols & their metabolites in animal samples with HPLC-EC*, J. Food Drug Anal. 1-12 (2017). The term "tocopherol" may be used herein to denote a liquid tocopherol or tocotrienol or derivative thereof as provided herein and suitable for use as described herein. In one embodiment, tocopherol is α-, β-, γ- or δ-tocopherol, or α-, β-, γ- or δ-tocotrienol. In another embodiment, the tocopherol is an α-, β-, γ-, or δ-tocopherol. In at least one embodiment, the tocopherol is tocopheryl acetate.

Additionally, the tocopherol component of the present embodiments remains in liquid form in the depot and does not undergo phase shift to solid, crystalline, or liquid crystalline form upon contact with water or aqueous bodily fluids, e.g., tears. Tocopherols are highly viscous liquids, and their ability to flow at different conditions related to temperature and flow velocity is a fundamental property of tocopherols.

In at least one embodiment, the tocopherol is tocopheryl acetate (also known as tocopherol acetate, vitamin E acetate, or "EA"), which is an ester of tocopherol and acetic acid. More specifically, tocopheryl acetate, IUPAC name "[(2R)-2,5,7,8-tetramethyl-2-[(4R,8R)-4,8,12-trimethyltridecyl] chroman-6-yl] acetate" (CAS Reg. No. 58-95-7), has low solubility in aqueous solution (having solubility in water of <0.1 g/100 mL at 17° C.), a viscosity of 6.31 Pa s to 6.59 Pa s (20° C.), and a refractive index of 1.496 n20/D. By comparison, the average refractive index values of human tears are about 1.33698. Craig et al., *Refractive index & osmolality of human tears,* 72(10) Optom. Vis. Sci. 718-24 (1995). In one embodiment, the tocopherol is tocopheryl acetate. In at least one embodiment, the liquid depot comprises any amount from 60% to 90%, inclusive, such as 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89% or 90% (wt %), tocopheryl acetate.

In addition to a tocopherol, the sustained-release liquid depot described herein includes an additional ocular film-former excipient, which in general terms is an excipient that is biocompatible and safe to use in the human eye, has low solubility in aqueous solution, does not impair vision (e.g., has a suitable refractive index at least in combination with tocopherol), and does not adversely affect either tocopherol stability in the eye or release of the pharmaceutical agent(s) from the liquid depot. It should be understood that although tocopherol is generally capable of forming a film in the eye and providing sustained release, tocopherol may be considered too viscous for practical use in the liquid depot described herein; the ocular film-forming excipient improves the spreadability or eases or hastens the application of the liquid depot described herein. In general, the ocular film-forming excipient renders the tocopherol less viscous. In other words, compared with tocopherol (e.g., tocopheryl acetate) as the sole component of a liquid depot, the additional ocular film-forming component provides a liquid depot that is comparatively less sticky, tacky, or viscous. This ocular film-forming excipient facilitates rapid and smooth coverage over the cornea, and also modifies the viscosity of the tocopherol component (e.g., tocopheryl acetate). It should be noted, however, that inclusion of too much film-forming excipient results in insufficient film depot and increases flushing of the active agent(s) from the eye.

Generally speaking, the ratio of tocopherol:film-forming excipient (e.g., wt/wt ratio) can be adjusted to modulate (e.g., increase or decrease) the sustained release profile of the liquid depot. For example, decreasing the amount of film-forming excipient generally increases the time in which the liquid depot stays in the eye and delivers active agent(s), i.e., increases the sustained release profile. Alternatively, or additionally, depending on the indication, the sustained release profile can be extended by increasing the amount of active agent(s) in the liquid depot. Further, depending on the indication, the concentration of active agent can be increased to increase the amount of active agent that is delivered to the back of the eye, i.e., the retina, by the liquid depot.

Thus, for example, a sustained-release liquid depot of the present embodiment that provides dexamethasone to the retina comprises, consists of, or consists essentially of (a) 10%-30% dexamethasone in (b) 70%-90% mixture of (i) tocopherol and (ii) film-forming excipient, in which the ratio of tocopherol:film-forming excipient is 85:15 to 70:10. In one embodiment, the amount of dexamethasone is about 10%: to increase the length of time or the amount of dexamethasone that is delivered to the retina, the amount of dexamethasone can be increased from about 10% to about 30% (or an interval therebetween); to increase the length of time that liquid depot delivers dexamethasone to the retina, the ratio of tocopherol:film-forming excipient can be adjusted from about 70:30 to about 85:15; and these options are not mutually exclusive such that both increasing the concentration of dexamethasone and decreasing the amount of film-forming excipient can be used to modulate the amount of dexamethasone delivered to the retina by the liquid depot. In general, the tocopherol and film-forming excipient remain in the liquid depot at roughly the same ratio during the course of delivery of dexamethasone to the retina.

Use of particular ocular film-forming excipients and the amount of each additional ocular film-former included in the sustained-release liquid depot described herein has been determined through laborious and detailed experiments to provide the type of excipient with the required characteristics and the amount needed to provide non-sticky, nearly immediate coating over the cornea with sufficient tocopherol to provide sustained release of pharmaceutical agent from the liquid depot. The required beneficial characteristics of the ocular film-forming excipient include safety for use in the eye, chemical and physical stability over an extended period of time, chemical compatibility with other formulation components, solubility in the formulation, ability to enhance the sustained release of the pharmaceutically active component, inertness, and the diffusion away from the liquid depot after exerting the desired effects.

Many potential film-forming excipients were considered or evaluated for inclusion in the liquid depot of the present embodiments, including castor oil, corn oil, triacetin, tributyrin, tricaprin, tricaprylin, water, dermol esters, benzoflex, polyethylene and polypropylene glycols, long chain aliphatic alcohols, hydroxypropyl methyl cellulose (HPMC), stearic acids, and stearic esters. These excipients did not, however, provide the multiple beneficial characteristics needed in order to progress through the rigorous evaluation processes employed to arrive at the liquid depot described herein. These excipients are not included in the liquid depot described herein.

In at least one embodiment, the ocular film-forming excipient is a mixture of triglycerides. In at least one embodiment, the ocular film-forming excipient is one or more medium-chain triglycerides (MCT). For example, mixed decanoyl and octanoyl glycerides (e.g., CAS 73398-61-5), comprise >95% saturated fatty acid chains, and are transparent, colorless or slightly yellow liquids, immiscible in water, practically odorless and tasteless, specific gravity of 0.94-0.96 (20° C.), refractive index of 1.440 to 1.452 n20D (20° C.), and viscosity ranging from 24 mPa s to 33 mPa s (20° C.) (14.9 cSt at 100° C.). Synonyms for MCT include decanoyl/octanoyl glycerides, mixed decanoate and octanoate triglycerides, glyceryl tricaprylate/caprate, oleum neutrale, Bergabest, Captex® 300, Captex® 355, Crodamol® GTCC, Labrafac® CC, MCT oil; MIGLYOL® 810; MIGLYOL® 812, Myritol Neobee® M5, Nesatol®, or Waglinol® 3/9280. Accordingly, the film-formers of the present embodiments may comprise triglycerides (and triglyceride-like) excipients, that include decanoyl/octanoyl glycerides (such as MIGLYOL® 810), caprylic/capric triglyceride (e.g., MIGLYOL® 812), and propylene glycol dicaprylate/dicaprate (triglyceride like) (e.g., MIGLYOL® 840), and mixtures thereof.

In exemplary embodiments, MIGLYOL®, combined with tocopherol, imparts the requisite beneficial characteristics to the liquid depot described herein, such as beneficial modulation of viscosity, flowability, inertness, transparency, solubility with other components (e.g., tocopherol and active agents), and permeability.

Accordingly, in one embodiment, the film-forming excipient is immiscible or has low solubility in water or aqueous solution. In one embodiment, the film-forming excipient has a viscosity of 27 mPa s to 33 mPa s (20° C.), inclusive, such as about 27, 28, 29, 30, 31, 32, or about 33 mPa s (20° C.), including intervals therebetween. In one embodiment, the film-forming excipient has a refractive index of 1.448 n20D to 1.451 n20D, such as about 1.448, 1.449, 1.450, or about 1.451 n20D, or intervals therebetween. In one embodiment, the film-forming excipient comprises, consists of, or consists essentially of decanoyl/octanoyl glycerides. In one embodiment, the decanoyl/octanoyl glycerides excipient is at least one of MIGLYOL® 810 or MIGLYOL® 812 (neutral oils). In at least one embodiment, the liquid depot includes any amount from 10% to 30%, inclusive, decanoyl/octanoyl glycerides, such as MIGLYOL® 810 or MIGLYOL® 812.

The liquid depot, when lacking a pharmaceutical agent (i.e., before an agent is loaded into the depot) may also be referred to as a blank, control, excipient component of a formulation, biodegradable excipient, excipient mixture, vehicle, and the like. The liquid depot remains in liquid state under physiologic conditions, both in vitro and in vivo, and does not polymerize or become solid after placement in the eye. This liquid depot can be loaded with highly concentrated active agent, but nevertheless remains liquid, safe and effective, while reducing side effects normally associated with the active agent administered in traditional eye drop formulations. Loading refers to any means by which at least one active agent is dispersed, dissolved, mixed, suspended, or otherwise incorporated into the liquid depot. Liquid refers generally to fluids, but also includes suspensions of solids dispersed in liquids (dispersions, suspensions, colloidal mixtures), and gasses dissolved in or otherwise present together within liquids, wherein fluidity of the liquid is maintained. The liquid depot of the present embodiments retains its fluid nature (i.e., does not solidify) before and after placement in the eye, and remains fluid as it biodegrades over time. Additionally, it is believed that the tocopherol and film-forming excipient remain in the liquid depot at roughly the same proportion (ratio) during the course of delivery of medicament to the retina.

In at least one embodiment, a single administration of the liquid depot, such as instillation of a liquid depot of about 20 $\mu m^3$ (20 $\mu L$) to about 70 $\mu m^3$ (70 $\mu L$) (such as about 20 $\mu L$, 25 $\mu L$, 30 $\mu L$, 35 $\mu L$, 40 $\mu L$, 45 $\mu L$, 50 $\mu L$, 55 $\mu L$, 60 $\mu L$, 65 $\mu L$, or about 70 $\mu L$, including intervals therebetween) provides for sustained release of a pharmaceutical agent to an interior tissue of the eye, such as the retina, for a period of at least about 3 days, at least about 4 days, at least about 5 days, at least about 6 days, at least about 1 week, at least about 2 weeks, or at least about 3 weeks, including intervals therebetween. In at least one embodiment, a single instillation of the liquid depot, such as a liquid depot of about 20 $\mu m^3$ (20 $\mu L$) to about 70 $\mu m^3$ (70 $\mu L$), inclusive, provides for sustained release of active agent to an interior tissue of the eye, such as the retina, for a period of at least about 24 hours, at least about 48 hours, at least about 72 hours (3 days), at least about 4 days, at least about 5 days, at least about 6 days, at least about 1 week (7 days), at least about 2 weeks (14 days), or at least about 3 weeks (21 days), including intervals therebetween.

Many pharmaceutical agents are suitable for sustained release from the liquid depot described herein. Such agents may have low solubility in water or aqueous solutions. For example, dexamethasone is safely and therapeutically delivered to the retina for a sustained period of time in an embodiment of the liquid depot described herein. In some embodiments, active agents are more stable in the liquid depot compared with the stability of those active agents in current aqueous-based eye drop formulations.

References to "pharmaceutical agent," "pharmaceutically active," "pharmaceutical," "drug," "medicament," "active agent," "active drug," "a bioactive agent" or a "therapeutic agent" and the like, refer in a general sense to substances useful in the medical and scientific arts, including, for example, drugs, biologics, diagnostic agents (e.g, dyes or contrast agents) or other substances used for therapeutic, preventative, diagnostic, or research purposes. Example pharmaceutical agents include biologics (e.g., insulin), chemotherapeutic agents, small molecules, antigens, interferons, polyclonal or monoclonal antibodies, anesthetics, interfering RNAs, gene vectors, contrast agents, or combinations of any of these. Reference to general or specific pharmaceutical agents or drugs includes pharmaceutically acceptable analogs, derivatives, and salts thereof. For example, reference to triamcinolone includes triamcinolone acetonide. Active agents that may be included in the liquid depots described herein are provided, for example, in U.S. Pat. No. 9,011,915.

"Inactive" substances typically refer to carriers, excipients, diluents, and the like, which are well-known in the art, although such substances may have beneficial function, such as, for example, stabilizing a pharmaceutical agent.

In one embodiment, an active agent is delivered to the eye in a manner that provides treatment or prevention (e.g., prophylaxis) of ocular disease in the back portion of the eye (posterior).

In some embodiments, the ocular tissue and fluids are in the back portion of the eye, such as the vitreous humor and retina.

In one embodiment, one application of the sustained-release liquid depot delivers active agent(s) to the back of the eye for at least 3 days.

In another aspect, methods of managing a clinical condition associated with or affecting the back of the eye are provided, comprising the intermittent administration (e.g., once every 1, 2, 3, 4, 5, 6, 7, 8, 9, or 10 days, once every 2 weeks, or once every 3 weeks) of a single dose of a medicament-containing liquid depot as described herein, wherein the dose is about 20 $\mu L$ to about 70 $\mu L$, inclusive and including volumes therebetween, such as, for example, 50 $\mu L$. It should further be understood that a single instillation might include two micro-drops (e.g., of 25 $\mu L$) instilled in rapid succession to provide a single one-time dose (e.g., of 50 $\mu L$). It should be understood that reference to intermittent dosing or dosage regimens reflects therapeutic dose over an extended period of time, such that administering once every three days or longer implies that sustained release has provided therapeutic effect such that more frequent administration is not indicated.

In one embodiment, the clinical condition is inflammation, such as, for example, cystoid macular edema. In one embodiment, the clinical condition is infection. It should be understood, however, that these indications may not be mutually exclusive; for example, infection is often associated with inflammation. Similarly, anti-infectives such as cyclosporine, are often administered to reduce inflammation. Accordingly, at least one embodiment provides a liquid depot formulation for prophylaxis of infection and inflammation, such as, for example, cystoid macular edema (CME) (that may be sequelae of cataract surgery).

In some embodiments, the sustained-release liquid depot comprises, as the pharmaceutical agent, a bioactive or therapeutic agent. Bioactive or therapeutic agents may have more than one activity or benefit, hence the following embodiments are not mutually exclusive. For example, anti-inflammatory steroids may have angiostatic activity as well. In some embodiments, the sustained-release liquid depot comprises at least one anti-inflammatory agent. In some embodiments, the sustained-release liquid depot comprises at least one anti-infective.

In another embodiment, the sustained-release liquid depot contains two or more different active agents, wherein at least one active provides benefit in treating a malady of the back of the eye. For example, in one embodiment each active agent selected for its ability to either stay associated with the cornea or pass through the cornea, such that one active agent stays on or in the cornea and the other active agent penetrates the interior of the eye to treat the retina. In one embodiment, the sustained-release liquid depot includes two or more active agents with similar capacities to penetrate the interior of the eye and to provide active agents to the retina.

An aspect of the present embodiments relates to a method of treating a disease or malady of the back of the eye, such as diabetic retinopathy, neovascular glaucoma, retinal vein occlusion, retinitis pigmentosa, macular degeneration (juvenile macular degeneration, age-related macular degeneration, wet macular degeneration, dry macular degeneration, or myopic macular degeneration), macular edema (or cystoid macular edema), central serous chorioretinopathy, choroidal folds, macular dystrophy (Stargardt's disease or fundus flavimaculatus, adult vitelliform, familial drusen, dominant cystoid macular edema, or cone degeneration), Best's disease (vitelliform macular dystrophy), idiopathic polypoidal choroidal vasculopathy, macular conditions arising in association with systemic problems (angioid streaks associated with pseudoxanthoma elasticum, Ehlers-Danlos syndrome, rarely Paget's disease of bone, and some haemoglobinopathies; cancer-related maculopathy; drug-induced maculopathies such as chloroquine- or hydroxychloroquine-induced retinotoxcity), or other retinal or vitreal conditions that benefit from topical delivery of medicament to the back of the eye. In at least one embodiment, the method of treating a malady of the back of the eye comprises applying a liquid depot comprising steroid(s) in tocopherol and MCT. In some embodiments, the steroid is dexamethasone or triamcinolone. Another embodiment provides a method of treating retinitis pigmentosa comprising application of a sustained-release liquid depot comprising valproic acid in tocopherol and MCT. In some embodiments, application of the liquid depot is intermittent, e.g., once every 1, 2, 3, 4, 5, 6, 7, 8, 9 or 10 days, once every 2 weeks, or once every 3 weeks.

At least one embodiment provides a sustained-release liquid depot that releases anti-glaucoma therapy. Anti-glaucoma active agents include inflow-suppressing/inhibiting agents, such as beta blocking agents (e.g., timolol, betaxolol, carteolol, levobunolol, etc.), topical carbonic anhydrase inhibitors (e.g., dorzolamide, brinzolamide), sympathomimetics (e.g., epinephrine, dipivefrin, clonidine, apraclonidine, brimonidine), outflow-facilitating agents including parasympathomimetics (e.g., cholinergic agonists such as pilocarpine), and prostaglandin analogues and related compounds (e.g., latanoprost, travoprost, bimatoprost, unoprostone, or tafluprost). Different pharmaceutical agents can be used alone or in combination to reduce intraocular pressure, including, for example, bimatoprost, latanoprost, travaprost, tafluprost, brimonidine, betaxolol, levobunolol, metipranolol, or timolol.

Accordingly, a specific embodiment is a liquid depot comprising tocopherol, ocular film-forming excipient, and timolol. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®)), and timolol.

Another specific embodiment is a liquid depot comprising tocopherol, ocular film-forming agent, and betaxolol. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and betaxolol.

Another specific embodiment is a liquid depot comprising tocopherol, ocular film-forming agent, and carteolol. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and carteolol.

Another specific embodiment is a liquid depot comprising tocopherol, ocular film-forming agent, and levobunolol. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and levobunolol.

Another specific embodiment is a liquid depot comprising tocopherol, ocular film-forming agent, and dorzolamide. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and dorzolamide.

Another specific embodiment is a liquid depot comprising tocopherol, ocular film-forming agent, and brinzolamide. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and brinzolamide.

Another specific embodiment is a liquid depot comprising tocopherol, ocular film-forming agent, and epinephrine. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and epinephrine.

Another specific embodiment is a liquid depot comprising tocopherol, ocular film-forming agent, and dipivefrin. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and dipivefrin.

Another specific embodiment is a liquid depot comprising tocopherol, ocular film-forming agent, and clonidine. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®) and clonidine.

Another specific embodiment is a liquid depot comprising tocopherol, ocular film-forming agent, and apraclonidine. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and apraclonidine.

Another specific embodiment is a liquid depot comprising tocopherol, ocular film-forming agent, and brimonidine. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and brimonidine.

Another specific embodiment is a liquid depot comprising tocopherol, ocular film-forming agent, and pilocarpine. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and pilocarpine.

Another specific embodiment is a liquid depot comprising tocopherol, ocular film-forming agent, and latanoprost. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and latanoprost.

Another specific embodiment is a liquid depot comprising tocopherol, ocular film-forming agent, and travoprost. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and travoprost.

Another specific embodiment is a liquid depot comprising tocopherol, ocular film-forming agent, and bimatoprost. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and bimatoprost.

Another specific embodiment is a liquid depot comprising tocopherol, ocular film-forming agent, and unoprostone. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and unoprostone.

Yet another specific embodiment is a liquid depot comprising tocopherol, ocular film-forming agent, and tafluprost. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and tafluprost.

At least one embodiment provides a sustained-release liquid depot that releases anti-inflammatory therapy, such as nonsteroidal anti-inflammatory drugs (NSAIDs), or steroidal anti-inflammatory, e.g., corticosteroids. The embodiments described herein support use of the liquid depot for a breadth of clinical indications for which anti-inflammatories are used. For example, although true anti-histamines are often used as anti-allergy eye drops, anti-inflammatories, including, e.g., loteprednol, are also used to alleviate allergies. For example, corticosteroids are used to treat allergic conjunctivitis. Indeed, the sustained-release liquid depot formulations comprising anti-inflammatory medicines as described herein may find clinical application in many different clinical indications, e.g., in treating or preventing: (a) inflammation associated with ocular surgery, including but not limited to, cataract surgery and vitrectomy, (b) uveitis, (c) diabetic macula edema (DME), (d) cystoid macula edema (CME), and (e) diabetic retinopathy.

In at least one embodiment, the sustained-release liquid depot includes a corticosteroid anti-inflammatory, such as, for example, dexamethasone, triamcinolone, prednisolone, prednisone, loteprednol, or fluorometholone, or pharmaceutically acceptable derivatives, analogs, and salts thereof or combinations thereof. Other anti-inflammatory agents that may be included in the sustained-release liquid depot described herein include angiostatic or anti-inflammatory steroids are known in the art.

Accordingly, a specific embodiment is a sustained-release liquid depot comprising tocopherol, ocular film-forming agent, and dexamethasone. An exemplary embodiment includes about 70% to 85% (wt %) tocopherol (such as tocopheryl acetate), about 15% to 30% (wt %) ocular film-forming excipient, such as decanoyl/octanoyl glycerides (e.g., MIGLYOL®), and dexamethasone. In some embodiments, the amount of dexamethasone is 10%-30% of the liquid depot. An exemplary embodiment provides a sustained-release liquid depot consisting of 30% (wt %) dexamethasone in 70% (wt %) of a mixture of tocopheryl acetate and MIGLYOL® at a tocopheryl acetate MIGLYOL® ratio of 70:30. An exemplary embodiment provides a sustained-release liquid depot consisting of 10% (wt %) dexamethasone in 90% (wt %) of a mixture of tocopheryl acetate and MIGLYOL® at a tocopheryl acetate MIGLYOL® ratio of 85:15. An exemplary embodiment provides a sustained-release liquid depot consisting of 30% (wt %) dexamethasone in 70% (wt %) of a mixture of tocopheryl acetate and MIGLYOL® at a tocopheryl acetate MIGLYOL® ratio of 85:15. These embodiments deliver a therapeutic dose of dexamethasone to the retina for at least about 3 days, at least about 7 days, or longer. In some embodiments, the topical administration of the sustained-release liquid depot comprising, consisting, or consisting essentially of (a) about 10-30% (wt %) dexamethasone and (b) about 70%-90% (wt %) of a mixture of tocopheryl acetate:medium chain triglycerides (at a wt/wt ratio of about 85:15 to about 70:30) to the retina of the subject may be indicated no more frequently than once every 3 days or once every 7 days.

Another specific embodiment is a sustained-release liquid depot comprising tocopherol, ocular film-forming agent, and prednisolone. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and prednisolone.

Another specific embodiment is a sustained-release liquid depot comprising tocopherol, ocular film-forming agent, and prednisone. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and prednisone.

Another specific embodiment is a liquid depot comprising tocopherol, ocular film-forming agent, and loteprednol. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and loteprednol.

Accordingly, a specific embodiment is a liquid depot comprising tocopherol, ocular film-forming agent, and fluorometholone. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and fluorometholone.

In at least one embodiment, the sustained-release liquid depot comprises a non-steroidal anti-inflammatory agent, such as, for example, ketorolac, nepafenac, bromfenac, or diclofenac, or combinations thereof.

Accordingly, in one embodiment, the liquid depot contains tocopherol, ocular film-forming excipient, and ketorolac. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and ketorolac.

In one embodiment, the liquid depot contains tocopherol, ocular film-forming agent, and nepafenac. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and nepafenac.

In another embodiment, the liquid depot contains tocopherol, ocular film-forming agent, and bromfenac. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and bromfenac.

In yet another embodiment, the liquid depot contains tocopherol, ocular film-forming agent, and diclofenac. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and diclofenac.

At least one embodiment provides a liquid depot for the sustained release of anti-infectives useful in treating or preventing intraocular infections. In at least one embodiment, the liquid depot comprises an anti-infective such as, for example, moxifloxacin, gatifloxacin, levofloxacin, ciprofloxacin, gentamicin, tobramycin, or chloramphenicol, or combinations thereof.

Accordingly, in one embodiment, the liquid depot contains tocopherol, ocular film-forming excipient, and moxifloxacin. An exemplary embodiment contains 10%-30% (wt %) moxifloxacin in 70%-90% (wt %) of a mixture of 65%-90% (wt %), tocopherol (such as tocopheryl acetate) and 10%-35% (wt %) ocular film-forming excipient, such as decanoyl/octanoyl glycerides (e.g., MIGLYOL®). In other words, this embodiment of a moxifloxacin liquid depot for the sustained release of moxifloxacin contains 10%-30% (wt %) moxifloxacin, 58.5%-81% tocopherol, and 9%-31.5% film-forming excipient.

In one embodiment, the liquid depot contains tocopherol, ocular film-forming agent, and gatifloxacin. An exemplary embodiment includes 10%-30% (wt %) gatifloxacin in 70%-90% (wt %) of a mixture of 65%-90% (wt %) tocopherol (such as tocopheryl acetate) and 10%-35% (wt %) ocular film-forming excipient, such as decanoyl/octanoyl glycerides (e.g., MIGLYOL®).

In one embodiment, the liquid depot contains tocopherol, ocular film-forming excipient, and levofloxacin. An exemplary embodiment contains levofloxacin in 70%-90% (wt %) of a mixture of about 65% to about 90% (wt %), inclusive, tocopherol (such as tocopheryl acetate), and about 10% to about 35% (wt %), inclusive, ocular film-forming excipient, such as decanoyl/octanoyl glycerides (e.g., MIGLYOL®).

In one embodiment, the liquid depot contains tocopherol, ocular film-forming agent, and ciprofloxacin. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and ciprofloxacin.

In another embodiment, the liquid depot contains tocopherol, ocular film-forming agent, and gentamicin. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and gentamycin.

In one embodiment, the liquid depot contains tocopherol, ocular film-forming agent, and tobramycin. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and tobramycin.

In yet another embodiment, the liquid depot contains tocopherol, ocular film-forming agent, and chloramphenicol. An exemplary embodiment includes about 70% to 80% (wt %) tocopherol (such as tocopheryl acetate), about 10% to 30% (wt %) ocular film-forming agent, such as fatty acid ester(s) (e.g., decanoyl/octanoyl glycerides), and chloramphenicol.

As noted above, anti-infectives such as cyclosporine are often administered to reduce inflammation. Accordingly, in at least one embodiment, the liquid depot comprises cyclosporine. An exemplary embodiment includes about 70% to 80% (wt %) tocopherol (such as tocopheryl acetate), about 10% to 30% (wt %) ocular film-forming excipient, such as decanoyl/octanoyl glycerides (e.g., MIGLYOL®), and cyclosporine.

At least one embodiment provides a liquid depot formulation for prophylaxis of infection and inflammation, such as cystoid macular edema (CME) or uveitis (both of which may be associated with cataract surgery).

Regarding uveitis, the uvea is the middle layer of the eye that contains much of the eye's blood vessels in addition to the iris, ciliary body, and choroid. Uveitis is a potentially blinding inflammation of this tissue, which disrupts vision by causing problems with the lens, retina, optic nerve, and vitreous. Uveitis can be anterior, intermediate, posterior or pan-uveitis, and is typically treated with steroids to reduce inflammation. A study comparing oral corticosteroids (prednisone) with a surgically implanted sustained release corticosteroid (0.59 mg fluocinolone acetonide intra-vitreous implant) revealed that although both treatments decreased inflammation in the eye, the corticosteroid implant produced more eye problems, such as cataracts, abnormally high intraocular pressure (IOP ≥21 mmHg), and glaucomatous optic nerve damage. Indeed, 69% of patients assigned to the implant required TOP lowering therapy, versus 26% of the systemic group; 15% versus 3% had an TOP spike to at least 40 mmHg; 23% versus 6% developed glaucomatous optic nerve damage; and 32% versus 5% required a surgical intervention. Importantly, the study concluded that TOP elevations in a substantial proportion of implanted patients would not be controllable with current eye drops therapy. Friedman et al., *Risk of elevated intraocular pressure & glaucoma in patients with uveitis; results of the Multicenter Uveitis Steroid Treatment Trial,* 120(8) Ophthalmol. 1571-79 (2013).

Regarding cataract, characterized by the development of lenticular opacities, cataract is a leading cause of blindness worldwide. Because adverse sequelae of cataract surgery include CME and uveitis, cataract surgeons often prescribe prophylactic administration of both steroidal and non-steroidal anti-inflammatory eye drops. Non-steroidal anti-inflammatory agents are included in prophylaxis to avoid long-term, high dose exposure to corticosteroids, which can cause elevated intraocular pressure and glaucoma as noted above. This combination is also prescribed to expose both anterior and posterior tissues to prophylaxis. Current eye drops formulations of corticosteroidal anti-inflammatory agents, however, raise IOP at least temporarily and in some patients IOP can remain above normal.

In contrast to the IOP sequelae described above, the dexamethasone-loaded liquid depot provided herein has not resulted in clinically significant elevated IOP. This result is surprising considering that current steroidal eye drops that raise IOP include only 0.1% (wt) corticosteroid, while, in contrast, the embodiments described herein can include 10% to 15% (wt %) corticosteroid (for example, dexamethasone). Importantly, as shown in the Examples herein, an embodiment liquid depot provides anti-inflammatory medicine to the retina (the back of the eye) for at least 7 days, such that prophylaxis against inflammatory conditions (e.g., uveitis) can be delivered to treat inflammation following cataract surgery. For example, a surgeon can apply the liquid depot following surgery, and one additional application is applied about 7 days (1 week) later to provide efficacious therapy and prophylaxis following cataract surgery. Also, importantly, the sustained delivery of anti-inflammatory medicine to the back of the eye may negate the need for use of both steroidal and nonsteroidal agents, replacing the nonsteroidal agent with a more efficacious steroidal dosage regimen.

In one embodiment, the sustained-release liquid depot consists of about 10% dexamethasone, about 30% dexamethasone, or from 10% to 30% dexamethasone, such as about 10%, 11%, 12%, 13%, 14%, 15%, 16%, 17%, 18%, 19%, 20%, 21%, 22%, 23%, 24%, 25%, 26%, 27%, 28%, 29%, or about 30% (wt %), or any interval therebetween, in a balance of a liquid mixture comprising, consisting of, or consisting essentially of about 70% to about 85% tocopherol (such as about 70%, 71%, 72%, 73%, 74%, 75%, 76%, 77%, 78%, 79%, 80%, 81%, 82%, 83%, 84%, or about 85% (% wt), or an interval therebetween) and 20% to 30% film-forming excipient(s) (such as about 15%, 16%, 17&, 18%, 19%, 20%, 21%, 22%, 23%, 24%, 25%, 26%, 27%, 28%, 29%, or about 30% (% wt) or an interval therebetween). In a specific embodiment, the tocopherol is tocopheryl acetate and the film-forming excipient is MIGLYOL® 810. In a specific embodiment, the tocopherol is tocopheryl acetate and the film-forming excipient is MIGLYOL® 812.

Further regarding film-forming excipients, MIGLYOL® 818 is a triglyceride of the fractionated $C_8$ and $C_{10}$ plant fatty acids (caprylic/capric/linoleic triglyceride); contains about 4%-5% linoleic acid; viscosity 30-35 mPa·s (20° C.); miscible in oils.

MIGLYOL® 810 (caprylic/capric triglyceride); caprylic:capric triglyceride ratio of 65%-80%:20%-35%, ≤2% caproic acid, ≤2% myristic acid; refractive index 1.448-1.451 n20D; viscosity about 27-33 m Pa s (20° C.); insoluble in water. In at least one embodiment, the film-forming excipient portion of the liquid depot is MIGLYOL® 810.

MIGLYOL® 812 (caprylic/capric triglyceride); caprylic:capric triglyceride ratio of 50%-65%:30%-45%, ≤2% caproic acid, ≤2% myristic acid; refractive index 1.448-1.451 n20D; viscosity 27-33 m Pa s (20° C.); insoluble in water. In at least one embodiment, the film-forming excipient portion of the liquid depot is MIGLYOL® 812. In at least one embodiment, the film-forming excipient portion of the liquid depot is a mixture of MIGLYOL® 810 and MIGLYOL® 812.

MIGLYOL® 829 (caprylic/capric/succinic triglyceride); caprylic/capric glyceride units crosslinked with succinic acid to form a larger molecule with unique properties; a glycerin ester of the fractionated $C_8$ and $C_{10}$ plant fatty acids, combined with succinic acid; viscosity is about 230 mPa·s (20° C.); high density of 1.00-1.02 g/cm$^3$ M (20° C.); virtually non-miscible in water.

MIGLYOL® 840, CAS #77466-09-2 is a propylene glycol diester of saturated plant fatty acids with chain lengths of $C_8$ and $C_{10}$; majority caprylic acid, less capric acid, small amounts of caproic, lauric, and myristic acids; density 0.91-0.93 g/cm$^3$ (20° C.); viscosity 9-12 mPa s (20° C.); refractive index 1.440-1.442 n20D; miscible in oils.

MYRITOL® 318 is a fatty acid triester with a refractive index of 1.4480-1.4500 dgf cIV 5, and a viscosity of 27-33 mPas (20° C.). MYRITOL® 318 comprises 33-41% $C_{24}$ ($C_8$ $C_8$); 41-46% $C_{26}$ ($C_8$ $C_{10}$+$C_8$ $C_{10}$ $C_8$); 13-19% $C_{18}$ ($C_{10}$ $C_8$+$C_{10}$ $C_8$ $C_{10}$); <4% $C_{30}$ ($C_{10}$ $C_{10}$ $C_{10}$).

Crodamol® GTCC or Crodamol® GTCC/C are fully saturated triesters, primarily caprylic/capric triglyceride, having a refractive index of 1.4485-1.4500 (n 20 D), low solubility in water, viscosity of 25-33 mPas (at 20° C.), and a relative density 0.93-0.96 g/cm$^3$ (g/mL).

Neobee® M5 is another fully saturated triester, primarily caprylic/capric triglyceride, having a refractive index of 1.4480-1.4510 (n 20 D), low solubility in water, viscosity of 25-33 mPas (20° C.), and relative density 0.94 g/cm$^3$ at 20° C.

Not all excipients are suitable film-forming agents for use in the embodiments described herein. For example, although cholesterol (CAS 57-88-5) has a refractive index of 1.53 n 20 D, low solubility in water, and is used as a nonionic emulsifier, and although cholesterol has been included with cyclodextrins or vaseline in preparations for treating dry eye, cholesterol was found unsuitable for use in a tocopherol-based liquid depot.

Further regarding tocopherols, α-Tocopherol: refractive index (RI) 1.503-1.507; practically insoluble in water; density 0.947-0.951 g/cm$^3$; oil. Tocopherols are incompatible with peroxides and metal ions, especially iron, copper, and silver; d-Alpha tocopherol: CAS 59-02-9; oil; d-α-tocopherol is the naturally occurring form of alpha-tocopherol; d-Alpha tocopheryl acetate: CAS 58-95-7; oil; dl-Alpha tocopheryl acetate: CAS 7695-91-21; RI 1.4950-1.4972; density 0.953 g/cm3, unstable to alkali, more stable than alpha-tocopherol, oil; Beta tocopherol: oil; CAS 148-03-8; Delta tocopherol: CAS 119-13-1; oil; Gamma tocopherol: CAS 7616-22-01; α-Tocotrienol: Refractive index: 1.523; β-Tocotrienol: Refractive index: 1.52, oil.

EXAMPLES

Example 1. Liquid Depot

Figure 2:
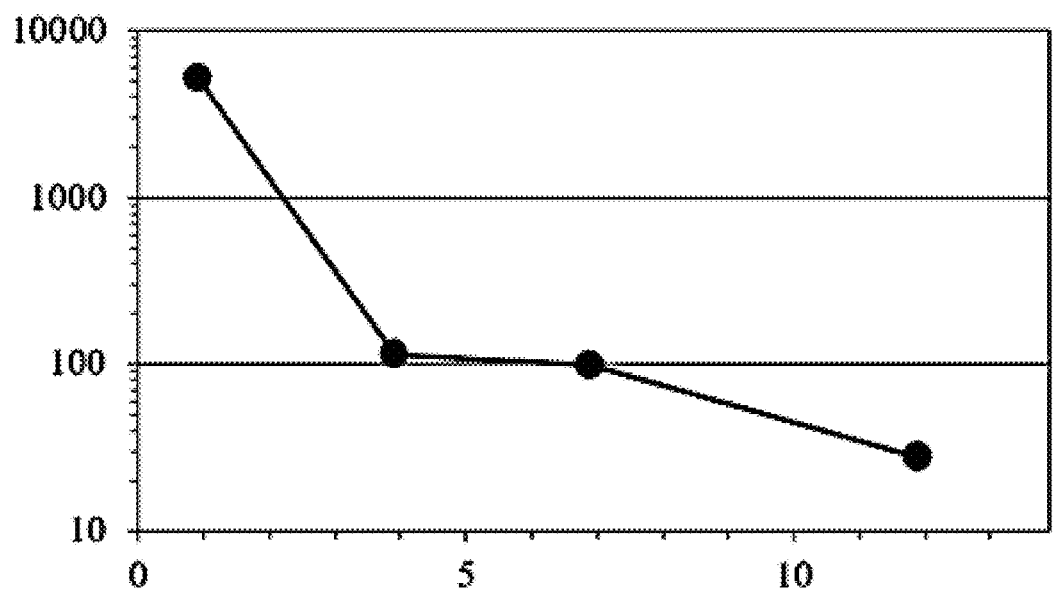
FIG. 2 shows the average amount of vitamin E acetate in tear samples collected from rabbit eyes on days 1, 4, 7, and 12 following administration of a single 50 µL depot of vitamin E acetate. During this same time course, vitamin E acetate was not observed in samples of aqueous humor. X-axis, days; y-axis, vitamin E acetate ng/mL.

To characterize a tocopherol-based liquid depot system, a single aliquot of 50 μL of vitamin E acetate was instilled into rabbit eyes. Subsequently, tear samples were collected using filter paper strips, and the vitamin E acetate contained in the paper strips extracted using methanol. The amount of vitamin E acetate in the methanol extracts was analyzed using LC/MS/MS by known methods. Vitamin E acetate was observed in tear samples collected on days 1, 4, 7, and 12, as shown in Table 1, and the results are shown graphically in FIG. 2.

TABLE 1

| Vitamin E acetate in rabbit tear sample from MeOH extract of paper strips | | |
|---|---|---|
| Day | Ave (ng/mL) | # of samples |
| 1 | 5249.50 | 4 |
| 4 | 114.13 | 4 |
| 7 | 98.63 | 4 |
| 12 | 27.40 | 6 |

Additionally, days 1, 4, 7, and 12, aqueous humor samples were collected from four eyes using syringes, then analyzed for the amount of vitamin E acetate in each sample using LC/MS/MC (quantification limit 1.0 ng/mL). No detectable vitamin E acetate was observed in aqueous humor samples on days 1, 4, 7, or 12.

The results show that measurable amounts of vitamin E acetate was present in the tears of rabbit eyes for at least 12 days, showing the liquid depot was present in the eye for at least 12 days despite normal lacrimal and eye functions; but vitamin E acetate was not present in the anterior chamber of the eye, showing that the liquid depot was not absorbed into the eye.

Example 2. Comparison of Dexamethasone In Vitro Release

Figure 3:
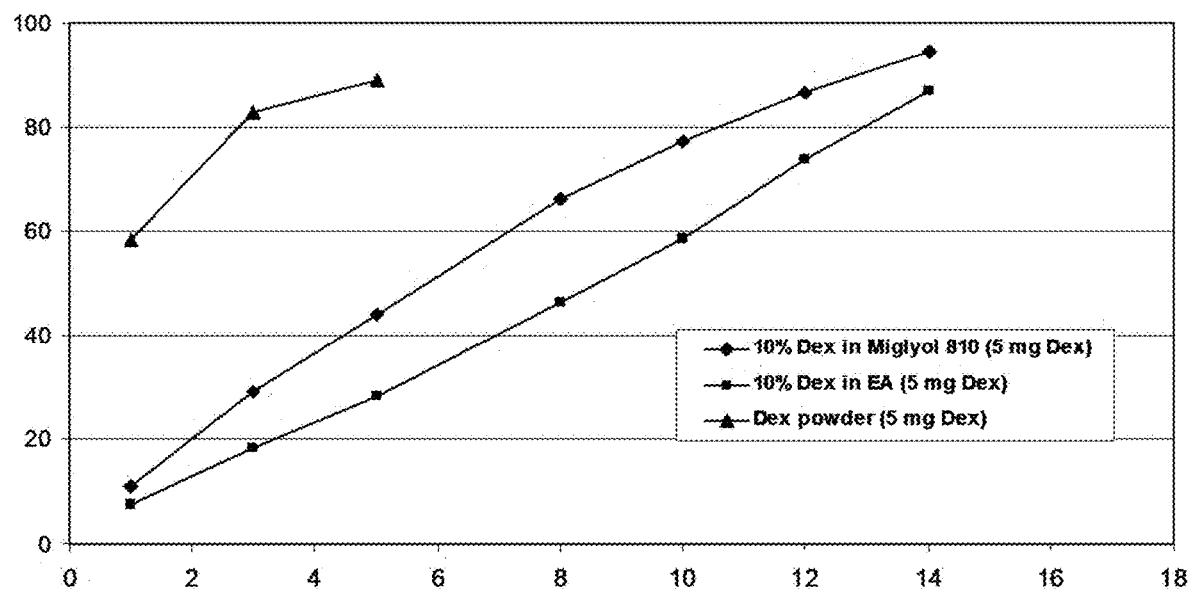
FIG. 3 is a graph showing in vitro release of 5 mg dexamethasone powder (▲), 5 mg dexamethasone in MIGLYOL® 810 (♦), or 5 mg dexamethasone in vitamin E acetate (■) in saline. Powder or 50 µL aliquots of liquid depot formulations were placed in 100 mL saline (50 mL exchange), and % dexamethasone release determined by UPLC. X-axis days; y-axis % total dexamethasone released into saline.

The percent dexamethasone released from 5 mg dexamethasone powder, 10% (5 mg) dexamethasone in MIGLYOL® 810, or 10% (5 mg) dexamethasone in tocopherol acetate was tested in a 100 mL saline sink (50 mL exchange). The results are shown graphically in FIG. 3.

Example 3. Liquid Depot Comprising Dexamethasone

Vitamin E is viscous, having a cP (mPas) of approximate 6000-6500 (20° C.). In combination with the liquid film-forming agent, MIGLYOL®, sustained release liquid depots comprising one or more of a number of pharmaceutical agents can be achieved. Miglyols are stable neutral oils that can be used as a carrier or solvent and are designated generally recognized as safe (GRAS) by the United States Food and Drug Administration.

Figure 4:
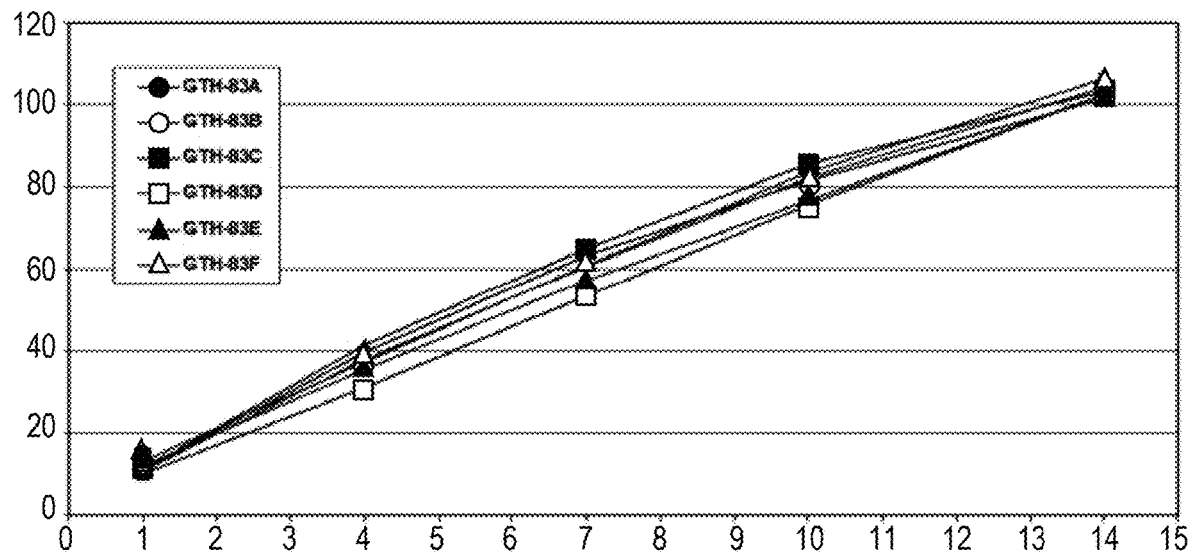
FIG. 4 is a graph showing in vitro release of dexamethasone from 50 µL aliquots of a liquid depot formulation (10% dexamethasone, 72% vitamin E acetate, and 18% MIGLYOL® 810 (medium chain triglycerides)), placed in 200 mL saline (100 mL exchange). Six replicates were tested: y-axis, % dexamethasone released; x-axis, days; ●: GTH-83A; ○: GTH-83B; ■: GTH-83C; □: GTH-83D; ▲: GTH-83E; Δ: GTH-83F.

A liquid depot was prepared by thoroughly mixing 10% dexamethasone, 72% vitamin E acetate, and 18% MIGLYOL® 810 (% in Examples refers to wt %). This dexamethasone-containing liquid depot had a viscosity of 850 cP-860 cP. A 50 μL aliquot was placed in 200 mL saline solution, then 100 mL withdrawn (and replaced with 100 mL fresh saline) at intervals, and the amount of dexamethasone determined by UPLC. The release profile of this formulation is shown in FIG. 4 (n=6, repetitions A-F); dexamethasone was released over ten days.

Another embodiment of a liquid depot was prepared by thoroughly mixing 10% dexamethasone, 72% vitamin E acetate, and 18% MIGLYOL® 810. The viscosity was measured in duplicate and indicated viscosity of 995 cP and 1008 cP (average 1001.5 cP); after three months, viscosity was measured at 1079 cP (average of all time points 1027 cP).

Example 4. Liquid Depot Delivery of Dexamethasone to the Interior of the Eye A liquid depot was assembled by thoroughly mixing 80 mg tocopheryl acetate with 20 mg MIGLYOL® 810 (neutral oil). Ten (10) mg dexamethasone was suspended in 90 mg of the liquid depot, and the formulation mixed to a homogeneous liquid. The dexamethasone liquid depot was sterilized by radiation using standard protocols.

One 25 μL unit of the dexamethasone-liquid depot was instilled into the eyes of female New Zealand White rabbits. Subsequently, the amount of dexamethasone present in the back of the eyes was determined at time points from 8 hours to 21 days. The data are shown in Table 2 (vitreous humor) and Table 3 (retina):

TABLE 2

Dexamethasone concentration (ng/mL, ng/g) vitreous humor

| | | | Vitreous Humor | |
|---|---|---|---|---|
| Time | ID | Eye | Conc. (ng/mL) | Average (±SD) |
| Hr 8 | 1 | OD | 34.3 | 31.5 ± 3.51 |
| | | OS | 33.0 | |
| | 2 | OD | 33.7 | |
| | | OS | 31.4 | |
| | 3 | OD | 30.7 | |
| | | OS | 24.7 | |
| Hr 24 | 4 | OD | 2.30 | 2.37 ± 0.893 |
| | | OS | 2.02 | |
| | 5 | OD | 3.53 | |
| | | OS | 3.36 | |
| | 6 | OD | 1.45 | |
| | | OS | 1.54 | |
| Day 3 | 7 | OD | 1.06 | 0.985 ± 0.342 |
| | | OS | 0.60 | |
| | 8 | OD | 0.855 | |
| | | OS | 0.772 | |
| | 9 | OD | 1.59 | |
| | | OS | 1.03 | |
| Day 8 | 10 | OD | BLOQ | ND |
| | | OS | 0.533 | |
| | 11 | OD | BLOQ | |
| | | OS | BLOQ | |
| | 12 | OD | BLOQ | |
| | | OS | BLOQ | |
| Day 14 | 13 | OD | BLOQ | ND |
| | | OS | BLOQ | |
| | 14 | OD | BLOQ | |
| | | OS | BLOQ | |
| | 15 | OD | BLOQ | |
| | | OS | BLOQ | |
| Day 21 | 16 | OD | BLOQ | ND |
| | | OS | BLOQ | |
| | 17 | OD | BLOQ | |
| | | OS | BLOQ | |

BLOQ: below limit of quantitation

TABLE 3

Dexamethasone concentration (ng/mL, ng/g) in retina

| | | | | | Retina | | |
|---|---|---|---|---|---|---|---|
| Time | ID | Eye | Tissue (g) | Homogenate (mL) | Homogenate (ng/mL) | Tissue (ng/g) | Average (±SD) |
| Hr 8 | 1 | OD | 0.087 | 0.434 | 19.0 | 95.0 | 110 ± 21.0 |
| | | OS | 0.061 | 0.304 | 23.0 | 115 | |
| | 2 | OD | 0.078 | 0.390 | 22.7 | 114 | |
| | | OS | 0.049 | 0.243 | 24.3 | 122 | |
| | 3 | OD | 0.058 | 0.292 | 15.6 | 78.0 | |
| | | OS | 0.036 | 0.180 | 27.6 | 138 | |
| Hr 24 | 4 | OD | 0.065 | 0.326 | 1.80 | 9.00 | 9.70 ± 3.81 |
| | | OS | 0.048 | 0.241 | 1.42 | 7.10 | |
| | 5 | OD | 0.072 | 0.358 | 3.31 | 16.6 | |
| | | OS | 0.054 | 0.273 | 2.14 | 10.7 | |
| | 6 | OD | 0.074 | 0.369 | 1.86 | 9.30 | |
| | | OS | 0.098 | 0.489 | 1.11 | 5.55 | |
| Day 3 | 7 | OD | 0.056 | 0.279 | 0.214 | 1.07 | 3.24 ± 1.69 |
| | | OS | 0.067 | 0.333 | 0.524 | 2.62 | |
| | 8 | OD | 0.064 | 0.322 | 0.720 | 3.60 | |
| | | OS | 0.056 | 0.278 | 0.466 | 2.33 | |
| | 9 | OD | 0.057 | 0.283 | 1.21 | 6.05 | |
| | | OS | 0.064 | 0.321 | 0.750 | 3.75 | |
| Day 8 | 10 | OD | 0.059 | 0.293 | 0.300 | 1.50 | 6.11 ± 5.50 |
| | | OS | 0.049 | 0.244 | 0.437 | 2.19 | |
| | 11 | OD | 0.090 | 0.450 | 0.276 | 1.38 | |
| | | OS | 0.077 | 0.383 | 3.04 | 15.2 | |
| | 12 | OD | 0.071 | 0.356 | 1.51 | 7.55 | |
| | | OS | 0.053 | 0.264 | 1.77 | 8.85 | |

TABLE 3-continued

Dexamethasone concentration (ng/mL, ng/g) in retina

Retina

| Time | ID | Eye | Tissue (g) | Homo-genate (mL) | Homo-genate (ng/mL) | Tissue (ng/g) | Average (±SD) |
|---|---|---|---|---|---|---|---|
| Day 14 | 13 | OD | 0.046 | 0.230 | BLOQ | ND | ND |
|  |  | OS | 0.060 | 0.300 | BLOQ | ND |  |
|  | 14 | OD | 0.072 | 0.358 | BLOQ | ND |  |
|  |  | OS | 0.063 | 0.313 | BLOQ | ND |  |
|  | 15 | OD | 0.056 | 0.283 | BLOQ | ND |  |
|  |  | OS | 0.067 | 0.333 | BLOQ | ND |  |
| Day 21 | 16 | OD | 0.06644 | 0.332 | BLOQ | ND | ND |
|  |  | OS | 0.073 | 0.363 | 0.579 | 2.90 |  |
|  | 17 | OD | 0.072 | 0.360 | BLOQ | ND |  |
|  |  | OS | 0.075 | 0.373 | BLOQ | ND |  |

Limit of quantitation: 0.5 ng/mL for humors, 0.2 ng/mL for tissues; BLOQ: below limit of quantitation;
Homog: homogenate; OD: right eye; OS: left eye; SD: standard deviation; ND: not determined.

These data show that one insertion of the liquid depot resulted in dexamethasone in the retina for at least 8 days (more than a week); and in the vitreous humor for at least three days.

Example 5. Liquid Depot Comprising Prednisolone

Figure 5:
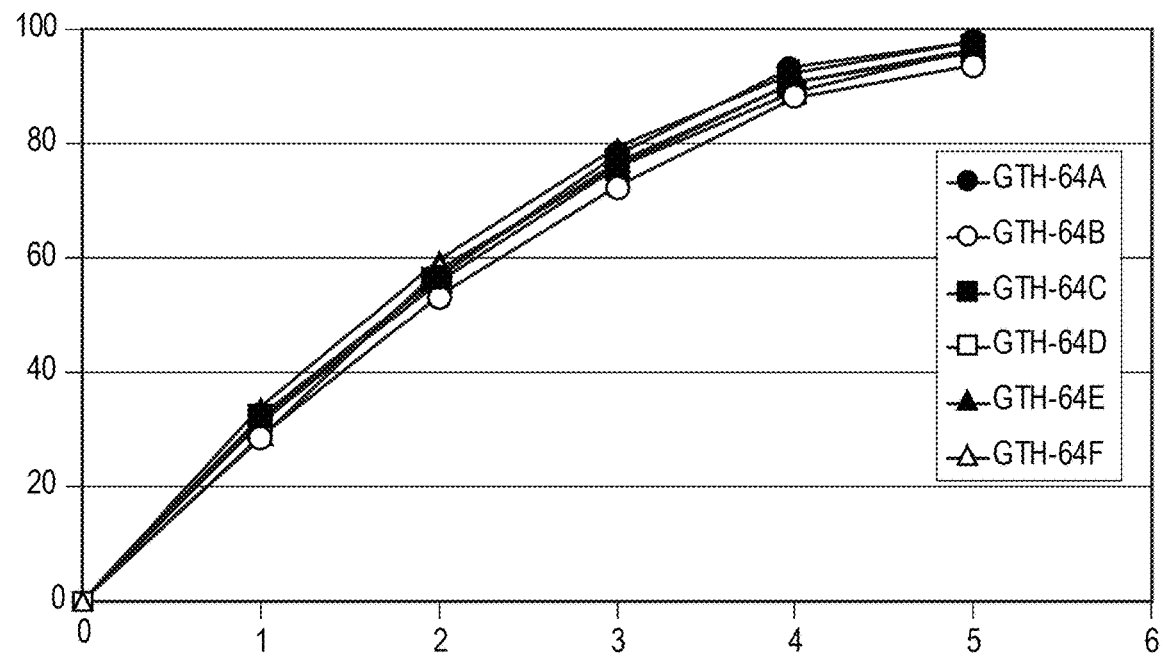
FIG. 5 is a graph showing in vitro release of prednisolone from a liquid depot formulation (10% prednisolone and 90% of a mixture of tocopheryl acetate:Miglyol® 810 (medium chain triglycerides) at a wt/wt ratio of about 80:20) placed in 100 gm water. For each time point, 60 ml sample was withdrawn for sampling and replaced with 60 mL saline. Six replicates were tested: y-axis, % prednisolone released; x-axis, days; ●: GTH-64A; ○: GTH-64B; ■: GTH-64C; □: GTH-64D; ▲: GTH-64E; Δ: GTH-64F.

A liquid depot was prepared by thoroughly mixing 10% prednisolone in an excipient mixture of 80% vitamin E acetate and 20% MIGLYOL® 810 (i.e., 10% prednisolone in 90% of a mixture of 80:20 tocopheryl acetate:MIGLYOL® 810). An in vitro sustained release study of prednisolone was carried out using Cabone rings (Wilton Brands LLC, Woodridge, Ill.) with an outer dimension (OD) of 0.5 inch and an inner dimension (ID) of 0.281 inch. Samples, GTH-64A to GTH-64F, each weighing at 50.9 mg, 48.6 mg, 50.4 mg, 48.7 mg, 51.6 mg, and 49.3 mg, respectively (average weight=49.92; SD=1.24; RSD (relative standard deviation)=2.47) were each separately added into a 125 mL urine sample cup (with cap) containing 100 gm of water. A 0.5" Cabone ring was placed inside the cup. At each time point, 60 ml from each of the six samples was withdrawn for sampling and replaced with 60 ml saline. The amount of prednisolone released was determined by UPLC. The release profile of prednisolone-containing liquid depot formulation is shown in Table 4 and FIG. 5; prednisolone was released for at least 5 days.

TABLE 4

Prednisolone cumulative % released

| Time (Days) | GTH-64A | GTH-64B | GTH-64C | GTH-64D | GTH-64E | GTH-64F | Avg | SD | % RSD |
|---|---|---|---|---|---|---|---|---|---|
| 0 | 0 | 0 | 0 | 0 | 0 | 0 | 0 |  |  |
| 1 | 32.3 | 28.7 | 31.4 | 33.9 | 31.1 | 28.5 | 31.0 | 2.1 | 6.8 |
| 2 | 56.9 | 53.5 | 57.3 | 59.9 | 56.1 | 58.1 | 57.0 | 2.1 | 3.7 |
| 3 | 78.2 | 72.7 | 76.8 | 79.6 | 75.9 | 76.2 | 76.6 | 2.3 | 3.0 |
| 4 | 93.5 | 88.1 | 90.8 | 92.4 | 89.2 | 90.6 | 90.7 | 2.0 | 2.2 |
| 5 | 97.9 | 93.8 | 95.9 | 97.8 | 96.3 | 96.4 | 96.4 | 1.5 | 1.6 |

Figure 6:
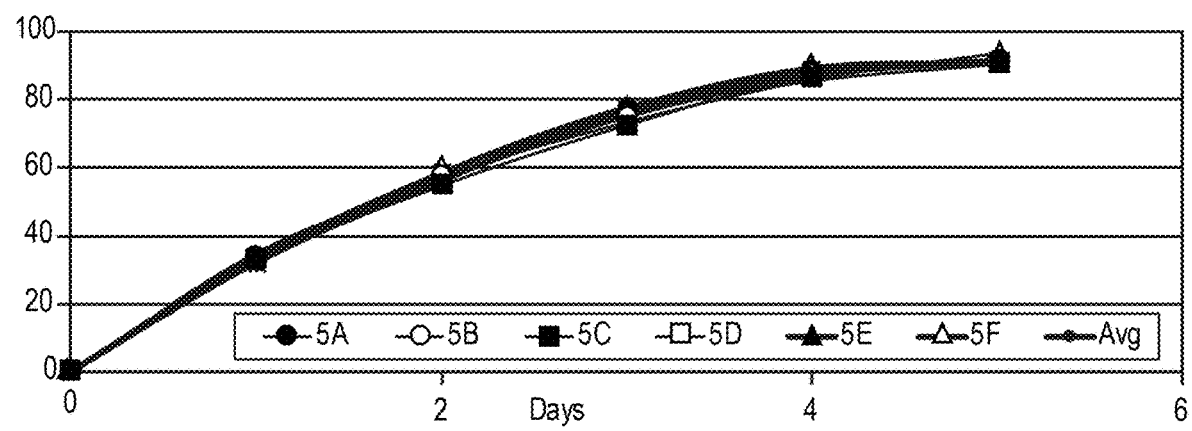
FIG. 6 is a graph showing in vitro release of prednisolone from a liquid depot formulation (10% prednisolone and 90% of a mixture of tocopheryl acetate:Miglyol® 810 (medium chain triglycerides) at a wt/wt ratio of about 80:20) that were placed in 100 gm water. For each time point, 50 ml sample was withdrawn for sampling and replaced with 50 mL saline. Six replicates were tested: y-axis, % prednisolone released; x-axis, days; ●: 5A; ○: 5B; ■: 5C; □: 5D; ▲: 5E; Δ: 5F; •: Avg.

Another prednisolone liquid depot was prepared by thoroughly mixing 10% prednisolone, 80% vitamin E acetate, and 20% Miglyol® 810 (10% prednisolone in 90% of a mixture of 80:20 tocopheryl acetate:Miglyol® 810). An in vitro sustained release study of prednisolone was carried out using a 12.7 mm Cabone ring. Six samples, 5A to 5F, each weighing at 48.2 mg, 48.5 mg, 48.1 mg, 49 mg, 51.7 mg, and 49.2 mg, respectively (average weight=49.1 mg; SD=1.34; % RSD=2.7) were incubated in 50 ml saline at 40° C. At each time point, 25 ml from each of the six samples was withdrawn for sampling and replaced with 25 ml saline. The amount of prednisolone released was determined by UPLC. The release profile of prednisolone-containing liquid depot formulation is shown in Table 5-Table 7 and FIG. 6; prednisolone was released for at least 5 days.

TABLE 5

Prednisolone cumulative % released

| Time (Days) | 5A | 5B | 5C | 5D | 5E | 5F | Avg | SD | % RSD |
|---|---|---|---|---|---|---|---|---|---|
| 0 | 0 | 0 | 0 | 0 | 0 | 0 | 0 |  |  |
| 1 | 34.8 | 32.5 | 32.6 | 33.9 | 31.9 | 33.5 | 33.2 | 1.1 | 3.2 |
| 2 | 56.9 | 56.6 | 54.8 | 57.2 | 56.0 | 58.5 | 56.7 | 1.3 | 2.2 |
| 3 | 76.5 | 75.4 | 72.5 | 73.4 | 77.0 | 77.7 | 75.4 | 2.1 | 2.8 |
| 4 | 88.0 | 85.1 | 86.8 | 85.9 | 88.9 | 88.4 | 87.2 | 1.5 | 1.7 |
| 5 | 92.0 | 90.0 | 91.9 | 93.6 | 90.6 | 91.6 | 91.6 | 1.2 | 1.4 |

TABLE 6

Amount of prednisolone released (µg)

| Time (Days) | 5A | 5B | 5C | 5D | 5E | 5F | Avg | SD | % RSD |
|---|---|---|---|---|---|---|---|---|---|
| 1 | 1678.5 | 1576.0 | 1568.0 | 1659.0 | 1650.0 | 1650.0 | 1630.3 | 46.4 | 2.8 |
| 2 | 1065.3 | 1167.0 | 1065.5 | 1145.0 | 1246.5 | 1229.5 | 1153.1 | 77.7 | 6.7 |
| 3 | 942.8 | 915.0 | 852.8 | 792.8 | 1086.3 | 944.8 | 922.4 | 99.5 | 10.8 |
| 4 | 556.0 | 471.3 | 689.3 | 611.5 | 612.0 | 525.0 | 577.5 | 76.6 | 13.3 |
| 5 | 64.1 | 79.3 | 82.3 | 126.3 | 29.3 | 52.3 | 72.3 | 32.8 | 45.4 |

TABLE 7

Average concentration of prednisolone released

| Time (Days) | Avg (µg/mL) | SD | % RSD |
|---|---|---|---|
| 1 | 32.6 | 0.9 | 2.8 |
| 2 | 39.4 | 1.7 | 4.3 |
| 3 | 38.1 | 2.6 | 6.8 |
| 4 | 30.6 | 1.7 | 5.6 |
| 5 | 19.6 | 1.7 | 8.6 |

Example 6. Liquid Depot Comprising Loteprednol

Figure 7:
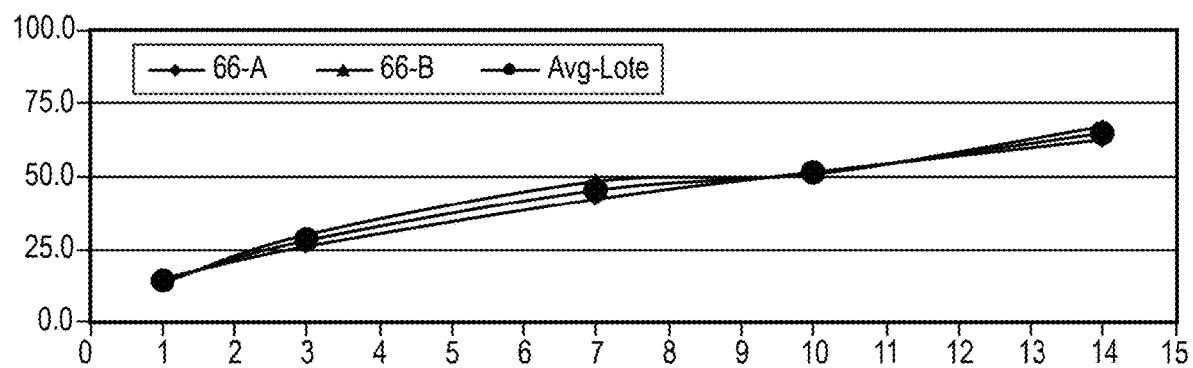
FIG. 7 is a graph showing in vitro release of loteprednol from a loteprednol-containing liquid depot formulation (10% loteprednol and 90% of a mixture of tocopheryl acetate:Miglyol® 810 (medium chain triglycerides) at a wt/wt ratio of about 80:20). Fifty mL of each sample were withdrawn for sampling and replaced with 50 mL of 40% methanol/water. Two replicates were tested: y-axis, % loteprednol released; x-axis, days; ●: 66-A; ○: 66-B; •: Avg.

A liquid depot was prepared by thoroughly mixing 10% loteprednol, 80% vitamin E acetate, and 20% MIGLYOL® 810, (10% loteprednol in 90% of a mixture of 80:20 tocopheryl acetate:MIGLYOL® 810). The in vitro sustained release study of loteprednol was carried out by incubating two samples, 66-A and 66-B, each weighing at about 71.8 mg and 59.8 mg, respectively in 100 mL of 40% methanol/water at 37° C. At each time point, 50 ml from each of the two samples was withdrawn for sampling and replaced with 50 mL of 40% methanol/water. The amount of loteprednol released was determined by UPLC. The release profile of loteprednol-containing liquid depot formulation is shown in Table 8, Table 9, and FIG. 7; loteprednol was released for at least 14 days.

TABLE 8

Average concentration of loteprednol released

| Sample ID | Day | µg/mL | µg/100 mL | Total Release | Release/day(µg) | Total release (%) |
|---|---|---|---|---|---|---|
| 66-A1 | 1 | 10.89 | 1089.0 | 1089.0 | 1089.0 | 15.2 |
| 66-A2 | 3 | 13.33 | 788.5 | 1877.5 | 394.3 | 26.1 |
| 66-A3 | 7 | 18.30 | 1163.5 | 3041.0 | 290.9 | 42.4 |
| 66-A4 | 10 | 15.80 | 665.0 | 3706.0 | 221.7 | 51.6 |
| 66-A5 | 14 | 15.85 | 795.0 | 4501.0 | 198.8 | 62.7 |
| 66-B1 | 1 | 8.12 | 812.0 | 812.0 | 812.0 | 13.6 |
| 66-B2 | 3 | 13.90 | 984.0 | 1796.0 | 492.0 | 30.0 |
| 66-B3 | 7 | 17.94 | 1099.0 | 2895.0 | 274.8 | 48.4 |
| 66-B4 | 10 | 10.45 | 148.0 | 3043.0 | 49.3 | 50.9 |
| 66-B5 | 14 | 14.93 | 970.5 | 4013.5 | 242.6 | 67.1 |

TABLE 9

Loteprednol cumulative % released

| Day | 66-A | 66-B | Avg | SD | % RSD |
|---|---|---|---|---|---|
| 1 | 15.2 | 13.6 | 14.4 | 1.1 | 7.8 |
| 3 | 26.1 | 30.0 | 28.1 | 2.7 | 9.8 |
| 7 | 42.4 | 48.4 | 45.4 | 4.3 | 9.4 |
| 10 | 51.6 | 50.9 | 51.3 | 0.5 | 1.0 |
| 14 | 62.7 | 67.1 | 64.9 | 3.1 | 4.8 |

Example 7. Liquid Depots Comprising Prednisone or Fluorometholone

Prednisone is loaded into a depot of tocopherol and MIGLYOL® as in Example 3. In vitro and in vivo sustained release data are collected as in Examples 3-4.

Fluorometholone is loaded into a depot of tocopherol and MIGLYOL® as in Example 3. In vitro and in vivo sustained release data are collected as in Examples 3-4.

Example 8. Liquid Depots Comprising Ciprofloxacin

Figure 8:
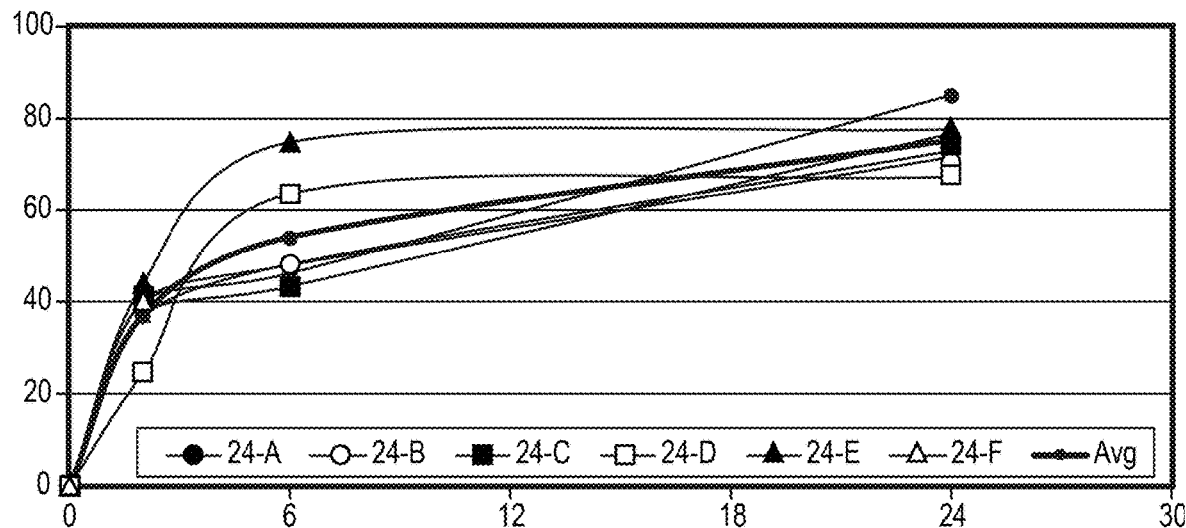
FIG. 8 is a graph showing in vitro release of ciprofloxacin from a ciprofloxacin-containing liquid depot formulation (15% ciprofloxacin and 85% of a mixture of tocopheryl acetate:Miglyol® 810 (medium chain triglycerides) at a wt/wt ratio of about 70:30). Twenty-five mL of each sample were withdrawn for sampling and replaced with 25 mL of saline. Six replicates were tested: y-axis, % ciprofloxacin released; x-axis, hours; ●: 24-A; ○: 24-B; ■: 24-C; □: 24-D; ▲: 24-E; Δ: 24-F; •: Avg.

A liquid depot was prepared by thoroughly mixing 15% ciprofloxacin hydrochloride, 70% vitamin E acetate, and 30% MIGLYOL® 810 (15% ciprofloxacin in 85% of a mixture of 70:30 tocopheryl acetate:MIGLYOL® 810). The in vitro sustained release study of ciprofloxacin was carried out using a 12.7 mm Cabone ring. Six samples, Cipro-24A to Cipro-24F, each weighing at 50.2 mg, 54.1 mg, 56.3 mg, 44 mg, 62.3 mg and 61 mg, respectively (average weight=54.65 mg; SD=6.857; % RSD=12.5) were incubated in 50 mL saline at 40° C. At each time point, 25 ml from each of the six samples was withdrawn for sampling and replaced with 25 mL saline. The amount of ciprofloxacin released was determined by UPLC. The release profile of ciprofloxacin-containing liquid depot formulation is shown in Table 10, Table 11, and FIG. 8; ciprofloxacin was released for at least 24 hours.

TABLE 10

Ciprofloxacin cumulative % released

| Time (Hours) | 24-A | 24-B | 24-C | 24-D | 24-E | 24-F | Avg | SD | % RSD |
|---|---|---|---|---|---|---|---|---|---|
| 0 | 0 | 0 | 0 | 0 | 0 | 0 | 0 | | |
| 2 | 36.5 | 40.1 | 37.4 | 24.4 | 44.1 | 40.0 | 37.1 | 6.7 | 18.2 |
| 6 | 48.1 | 47.9 | 43.3 | 63.5 | 75.0 | 46.2 | 54.0 | 12.5 | 23.1 |
| 24 | 73.0 | 71.5 | 76.7 | 67.2 | 77.8 | 85.2 | 75.2 | 6.2 | 8.2 |

TABLE 11

Average concentration of ciprofloxacin released

| Time (Hours) | Avg (ug/mL) | SD | % RSD |
|---|---|---|---|
| 2 | 61.8 | 17.2 | 27.9 |
| 6 | 57.7 | 22.3 | 38.6 |
| 24 | 64.5 | 19.6 | 30.3 |

Example 9. Liquid Depot Comprising Ciprofloxacin

Figure 9:
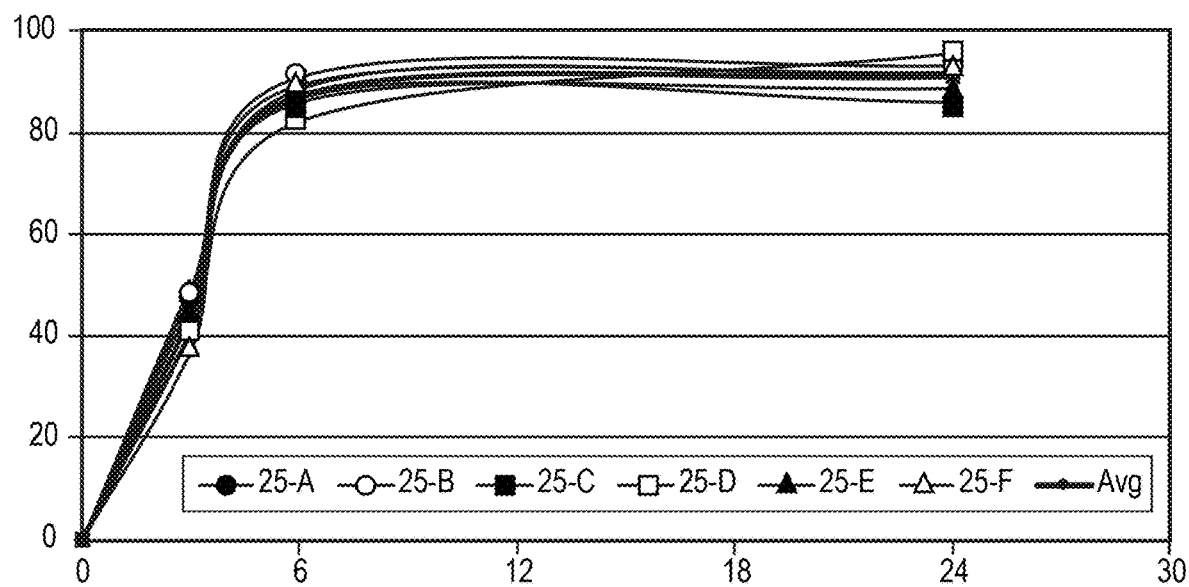
FIG. 9 is a graph showing another in vitro release of ciprofloxacin from a ciprofloxacin-containing liquid depot formulation (15% ciprofloxacin and 85% of a mixture of tocopheryl acetate:Miglyol® 810 (medium chain triglycerides) at a wt/wt ratio of about 70:30). Twenty-five mL of each sample were withdrawn for sampling and replaced with 25 mL of saline. Six replicates were tested: y-axis, % ciprofloxacin released; x-axis, hours; ●: 25-A; α3: 25-B; ■: 25-C; □: 25-D; ▲: 25-E; Δ: 25-F; •: Avg.

Another liquid depot comprising ciprofloxacin similar to Example 8 was prepared by thoroughly mixing 15% ciprofloxacin hydrochloride, 70% vitamin E acetate, and 30% MIGLYOL® 810, (15% ciprofloxacin in 85% of a mixture of 70:30 tocopheryl acetate:MIGLYOL® 810). The in vitro sustained release study of ciprofloxacin was carried out using a 12.7 mm Cabone ring. Six samples, Cipro-25A to Cipro-25F, each weighing at 45.8 mg, 48.5 mg, 51.2 mg, 48 mg, 62.2 mg and 49.3 mg, respectively (average weight=50.83 mg; SD=5.839; % RSD=11.5) were incubated in 50 mL saline at 40° C. At each time point, 25 ml from each of the six samples was withdrawn for sampling and replaced with 25 mL saline. The amount of ciprofloxacin released was determined by UPLC. The release profile of ciprofloxacin-containing liquid depot formulation is shown in Table 12, Table 13, and FIG. 9; ciprofloxacin was released for at least 24 hours.

TABLE 12

Ciprofloxacin cumulative % released

| Time (Hours) | 25-A | 25-B | 25-C | 25-D | 25-E | 25-F | Avg | SD | % RSD |
|---|---|---|---|---|---|---|---|---|---|
| 0 | 0 | 0 | 0 | 0 | 0 | 0 | 0 | | |
| 3 | 49.6 | 48.0 | 40.5 | 40.9 | 45.9 | 37.0 | 43.7 | 4.9 | 11.3 |
| 6 | 89.3 | 90.8 | 86.7 | 82.2 | 85.7 | 88.7 | 87.2 | 3.1 | 3.5 |
| 24 | 91.8 | 93.0 | 86.0 | 95.5 | 88.4 | 91.4 | 91.0 | 3.4 | 3.7 |

TABLE 13

Average concentration of ciprofloxacin released

| Time (Hours) | Avg (ug/mL) | SD | % RSD |
|---|---|---|---|
| 3 | 66.6 | 10.9 | 16.4 |
| 6 | 99.6 | 10.7 | 10.7 |
| 24 | 55.5 | 6.9 | 12.4 |

Example 10. Liquid Depots Comprising Gatifloxacin

A liquid depot was prepared by thoroughly mixing 10% gatifloxacin, 70% vitamin E acetate, and 30% MIGLYOL® 810, (10% gatifloxacin in 90% of a mixture of 70:30 tocopheryl acetate:MIGLYOL® 810). The in vitro sustained release study of gatifloxacin was carried out using a Cabone ring (Wilton Brands LLC, Woodridge, Ill. 60517) of 12.7 mm. Six samples, Gati-90A to Gati-90F, each weighing at 48.2 mg, 48 mg, 48.9 mg, 47 mg, 49.1 mg, and 47.8 mg, respectively (average weight=48.17 mg; SD=0.766; % RSD=1.6) were incubated in 40 mL saline at 40° C. At each time point, 20 ml from each of the six samples was withdrawn for sampling and replaced with 20 mL saline. The amount of gatifloxacin released was determined by UPLC. The release profile of gatifloxacin-containing liquid depot formulation is shown in Table 14, Table 15, and FIG. 10; gatifloxacin was released for at least 24 hours.

TABLE 14

Gatifloxacin cumulative % released

| Time (Hours) | 90-A | 90-B | 90-C | 90-D | 90-E | 90-F | Avg | SD | % RSD |
|---|---|---|---|---|---|---|---|---|---|
| 1 | 30.7 | 33.7 | 32.5 | 29.7 | 35.8 | 31.2 | 32.3 | 2.2 | 6.9 |
| 3 | 68.8 | 70.8 | 67.2 | 60.4 | 73.1 | 65.1 | 67.5 | 4.5 | 6.6 |
| 24 | 81.7 | 88.9 | 84.4 | 84.0 | 92.3 | 85.9 | 86.2 | 3.8 | 4.4 |

TABLE 15

Average concentration of gatifloxacin released

| Time (Hours) | Avg µg/mL | SD | % RSD |
|---|---|---|---|
| 1 | 38.9 | 3.2 | 8.2 |
| 3 | 61.9 | 5.0 | 8.1 |
| 24 | 53.4 | 3.2 | 6.0 |

Example 11. Liquid Depots Comprising Anti-Infectives

Moxifloxacin is loaded into a depot of tocopherol and MIGLYOL® as in Example 3. In vitro and in vivo sustained release data are collected as in Examples 3-4.

Levofloxacin is loaded into a depot of tocopherol and MIGLYOL® as in Example 3. In vitro and in vivo sustained release data are collected as in Examples 3-4.

Gentamicin is loaded into a depot of tocopherol and MIGLYOL® as in Example 3. In vitro and in vivo sustained release data are collected as in Examples 3-4.

Tobramycin is loaded into a depot of tocopherol and MIGLYOL® as in Example 3. In vitro and in vivo sustained release data are collected as in Examples 3-4.

Chloramphenicol is loaded into a depot of tocopherol and MIGLYOL® as in Example 3. In vitro and in vivo sustained release data are collected as in Examples 3-4.

Example 12. Liquid Depot Comprising a NSAID

A formulation of the NSAID diclofenac was prepared by thoroughly mixing 10% diclofenac acid in a 90% liquid depot mixture of 80:20 tocopheryl acetate:Miglyol®. A one-time application of 50 µL of this formulation was instilled into the eyes of NZW rabbits, and then tear samples were collected and analyzed as described herein. The results, as shown in FIG. 11, indicate that diclofenac was detected in the rabbit tear film for a least 7 days.

Example 13. Liquid Depot Comprising Cyclosporin

Two formulations comprising 2% cyclosporin A (CsA) were prepared as provided herein. One formulation contained 2% CsA in a mixture of 90:10 tocopheryl acetate:Miglyol® 812; the other contained 2% CsA in a mixture of 70:30 tocopheryl acetate:Miglyol® 812. The in vitro release (% CsA release) was monitored as described herein, and the total % release of CsA plotted over the course of at least 120 days, as shown in FIG. 12.

Example 14. Liquid Depot Applications

A sustained-release liquid depot loaded with a therapeutic agent is administered as a single application or provided in the form of a kit to a subject who wears contact lens or make up. Because of the physical consistency, no running of the liquid depot is observed in the subject's eyes. In addition, the subject does not experience blurring of vision or eye irritation. Accordingly, at least one embodiment provides a kit comprising at least one single-use dispenser, wherein the at least one single-use dispenser comprises the liquid depot as described herein.

What is claimed is:

1. A method of treating the retina in an eye of a subject, comprising topically administering to the eye of the subject a liquid depot comprising: (a) about 10%-15% (wt %)

dexamethasone; and (b) about 85%-90% (wt %) of a mixture of tocopheryl acetate:medium-chain triglycerides at a wt/wt ratio of about 70:30 to about 80:20, wherein the medium chain triglycerides are medium chain triglycerides or triglyceride-like excipients selected from the group consisting of caprylic/capric triglycerides and decanoyl/octanoyl glycerides; and wherein the liquid depot has a viscosity of about 850 to about 1100 cP.

2. The method of claim 1, wherein the liquid depot comprises (a) about 10% dexamethasone; and (b) about 90% of a mixture of tocopheryl acetate:medium-chain triglycerides at a wt/wt ratio of about 70:30 to about 80:20.

3. The method of claim 1, wherein the liquid depot comprises (a) about 10% dexamethasone; and (b) about 90% of a mixture of tocopheryl acetate:medium-chain triglycerides at a wt/wt ratio of about 70:30.

4. The method of claim 1, wherein the liquid depot comprises (a) about 15% dexamethasone; and (b) about 85% of a mixture of tocopheryl acetate:medium-chain triglycerides at a wt/wt ratio of about 70:30 to about 80:20.

5. The method of claim 1, wherein said administering is intermittent.

6. The method of claim 5, wherein said intermittent administration is for at least about 24 hours, 48 hours, 72 hours (3 days), 4 days, 5 days, 6 days, 7 days (1 week), 14 days (2 weeks), or 21 days (3 weeks).

7. The method of claim 1, wherein said administering is no more frequently than once every three (3) days.

8. The method of claim 1, wherein said administering is no more frequently than once every seven (7) days.

9. The method of claim 1, wherein the medium chain triglyceride-like excipient is decanoyl/octanoyl glycerides.

10. The method of claim 1, wherein the medium chain triglyceride is caprylic/capric triglyceride.

11. The method of claim 1, wherein the liquid depot comprises (a) about 10% dexamethasone; and (b) about 90% of a mixture of tocopheryl acetate:medium-chain triglycerides at a wt/wt ratio of about 80:20.

* * * * *